US010768783B2

(12) United States Patent
Lee et al.

(10) Patent No.: US 10,768,783 B2
(45) Date of Patent: Sep. 8, 2020

(54) METHOD AND APPARATUS FOR PROVIDING APPLICATION INFORMATION

(71) Applicant: Samsung Electronics Co., Ltd., Gyeonggi-do (KR)

(72) Inventors: Kyung-Hee Lee, Gyeonggi-do (KR); Chang-Ryong Heo, Gyeonggi-do (KR); Ken-Hyung Park, Gyeonggi-do (KR); Chi-Hyun Cho, Gyeonggi-do (KR); Kun-Woo Baek, Gyeonggi-do (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 502 days.

(21) Appl. No.: 14/539,821

(22) Filed: Nov. 12, 2014

(65) Prior Publication Data

US 2015/0135086 A1    May 14, 2015

(30) Foreign Application Priority Data

Nov. 12, 2013    (KR) .................. 10-2013-0136773

(51) Int. Cl.
*G06F 3/0482*    (2013.01)
*G06F 3/0488*    (2013.01)
(Continued)

(52) U.S. Cl.
CPC .......... *G06F 3/0482* (2013.01); *G06F 3/0486* (2013.01); *G06F 3/0488* (2013.01); *G06F 3/04847* (2013.01); *G06F 2203/04803* (2013.01)

(58) Field of Classification Search
CPC ............... G06F 3/0482; G06F 3/04846; G06F 3/04847; G06F 3/0488
See application file for complete search history.

(56) References Cited

U.S. PATENT DOCUMENTS 5,757,371 A * 5/1998 Oran .................... G06F 3/0482
715/779
6,100,887 A * 8/2000 Bormann ............ G06F 3/04847
345/440

(Continued)

FOREIGN PATENT DOCUMENTS

CN    102695151 A    9/2012
EP    2194698 A1    6/2010
(Continued)

OTHER PUBLICATIONS

International Search Report dated Feb. 4, 2015 in connection with International Application No. PCT/KR2014/010771; 3 pages.
(Continued)

*Primary Examiner* — Ryan Barrett

(57) ABSTRACT

A method for providing application information in an electronic device includes providing at least one application item including information regarding a corresponding application, by using a first specified area of a display operatively coupled to an electronic device, identifying or selecting at least one item from the at least one application item, providing execution information of an application corresponding to the at least one item via a second specified area of the display based on the identifying, and providing additional information related to the execution information via the first specified area, based on the execution information. Other embodiments are also possible.

14 Claims, 13 Drawing Sheets

(51) Int. Cl.
G06F 3/0486 (2013.01)
G06F 3/0484 (2013.01)

(56) References Cited

U.S. PATENT DOCUMENTS

| | | | |
|---|---|---|---|
| 6,477,117 B1 | 11/2002 | Narayanaswami et al. | |
| 8,019,389 B2 | 9/2011 | Kim et al. | |
| 8,369,898 B2 | 2/2013 | Chun | |
| 8,624,836 B1* | 1/2014 | Miller | G06F 1/163 345/157 |
| 8,793,606 B2 | 7/2014 | Kim | |
| 8,847,545 B2 | 9/2014 | Williams | |
| 8,860,674 B2 | 10/2014 | Lee et al. | |
| 8,974,349 B2 | 3/2015 | Weast et al. | |
| 10,185,416 B2 | 1/2019 | Mistry et al. | |
| 2003/0117440 A1* | 6/2003 | Hellyar | G06F 3/0235 715/767 |
| 2003/0142109 A1* | 7/2003 | Brown | G06F 3/0481 345/592 |
| 2005/0091596 A1* | 4/2005 | Anthony | G06F 3/04815 715/712 |
| 2005/0168488 A1* | 8/2005 | Montague | G06F 3/04845 345/659 |
| 2006/0123353 A1* | 6/2006 | Matthews | G06F 3/0481 715/779 |
| 2006/0224989 A1* | 10/2006 | Pettiross | G06F 3/0483 715/779 |
| 2006/0242602 A1* | 10/2006 | Schechter | G06F 3/04817 715/838 |
| 2007/0252822 A1 | 11/2007 | Kim et al. | |
| 2008/0005679 A1 | 1/2008 | Rimas-Ribikauskas et al. | |
| 2008/0082937 A1* | 4/2008 | Bennah | G06F 3/0481 715/781 |
| 2008/0143685 A1 | 6/2008 | Lee et al. | |
| 2008/0222569 A1* | 9/2008 | Champion | G06F 3/0482 715/834 |
| 2008/0259045 A1* | 10/2008 | Kim | G06F 3/0486 345/173 |
| 2009/0070695 A1* | 3/2009 | Oh | G06F 3/0486 715/769 |
| 2009/0183100 A1 | 7/2009 | Eom et al. | |
| 2009/0193364 A1* | 7/2009 | Jarrett | G06F 3/04817 715/838 |
| 2009/0199127 A1* | 8/2009 | Sareen | G06F 3/0481 715/781 |
| 2009/0235200 A1* | 9/2009 | Deutsch | G06F 9/4443 715/783 |
| 2010/0107115 A1* | 4/2010 | Sareen | G06F 3/0481 715/783 |
| 2010/0107123 A1* | 4/2010 | Sareen | G06F 3/0481 715/835 |
| 2010/0192103 A1* | 7/2010 | Cragun | G06F 3/04817 715/834 |
| 2010/0257482 A1* | 10/2010 | Lyons | G06F 3/0486 715/794 |
| 2011/0157046 A1 | 6/2011 | Lee et al. | |
| 2011/0251822 A1 | 10/2011 | Darley et al. | |
| 2012/0035881 A1 | 2/2012 | Rubin et al. | |
| 2012/0066629 A1* | 3/2012 | Lee | G06F 3/04847 715/769 |
| 2012/0117499 A1 | 5/2012 | Mori et al. | |
| 2012/0124515 A1* | 5/2012 | Li | G06F 3/0482 715/808 |
| 2012/0229521 A1* | 9/2012 | Hales, IV | G05D 23/1917 345/684 |
| 2012/0252532 A1 | 10/2012 | Williams | |
| 2012/0296959 A1* | 11/2012 | Momchilov | G06F 9/54 709/203 |
| 2013/0040567 A1* | 2/2013 | Matsubara | G06F 3/0488 455/41.1 |
| 2013/0073364 A1* | 3/2013 | Jung | G06Q 30/02 705/14.23 |
| 2013/0080975 A1* | 3/2013 | Geithner | G06F 3/0488 715/828 |
| 2013/0115583 A1 | 5/2013 | Gordon et al. | |
| 2013/0138230 A1* | 5/2013 | Landers | G06F 17/40 700/91 |
| 2013/0212487 A1* | 8/2013 | Cote | G06F 3/048 715/745 |
| 2014/0180595 A1* | 6/2014 | Brumback | A61B 5/0015 702/19 |
| 2015/0040069 A1* | 2/2015 | Gunaratnam | G06F 3/04817 715/834 |
| 2015/0169838 A1* | 6/2015 | Simon | G16H 50/30 702/19 |
| 2015/0301691 A1* | 10/2015 | Qin | G11B 27/105 715/772 |
| 2015/0363065 A1* | 12/2015 | Kim | G06F 3/0482 715/739 |
| 2016/0188152 A1* | 6/2016 | Chou | G06F 3/0488 345/173 |
| 2016/0259491 A1* | 9/2016 | Jacobs | G06F 3/0481 |
| 2016/0320909 A1* | 11/2016 | Eim | G06F 1/163 |
| 2016/0327915 A1* | 11/2016 | Katzer | G04B 19/04 |

FOREIGN PATENT DOCUMENTS

| | | |
|---|---|---|
| EP | 2284674 A2 | 2/2011 |
| KR | 10-2007-0075153 | 7/2007 |
| KR | 10-2009-0048803 A | 5/2009 |
| KR | 10-2010-0048297 | 5/2010 |
| KR | 10-2011-0008939 | 1/2011 |
| KR | 10-2015-0029453 A | 3/2015 |
| WO | 2007069835 A1 | 6/2007 |

OTHER PUBLICATIONS

Written Opinion of International Searching Authority dated Feb. 4, 2015 in connection with International Application No. PCT/KR2014/010771; 6 pages.
European Patent Office, "Supplementary Search Report," Application No. EP 14 86 1802, dated Jun. 2, 2017, 13 pages.
Communication from a foreign patent office in a counterpart foreign application, European Patent Office, "Communication pursuant to Article 94(3) EPC," Application No. EP 14861802.8, dated Apr. 13, 2018, 12 pages.
Communication from a foreign patent office in a counterpart foreign application, The State Intellectual Property Office of the People's Republic of China, "The First Office Action," Application No. CN 201480061669A, dated Jun. 5, 2018, 42 pages.
Summons to attend oral proceedings pursuant to Rule 115(1) EPC dated Mar. 6, 2019 in connection with European Patent Application No. 14 861 802.8, 11 pages.
China National Intellectual Property Administration, "The Third Office Action," Application No. CN201480061669.X, dated Jul. 9, 2019, 27 pages.
Provision of the minutes in accordance with Rule 124(4) EPC dated Nov. 12, 2019 in connection with European Patent Application No. 14 861 802.8, 7 pages.
Decision to refuse a European Patent application dated Nov. 18, 2019 in connection with European Patent Application No. 14 861 802.8, 27 pages.
Result of consultation dated Oct. 8, 2019 in connection with European Patent Application No. 14 861 802.8, 4 pages.
European Search Report dated Apr. 7, 2020 in connection with European Patent Application No. 19 20 0845, 11 pages.
Office Action dated Jan. 21, 2020 in connection with Chinese Patent Application No. 201480061669.X, 30 pages.
Office Action dated Mar. 2, 2020 in connection with Korean Patent Application No. 10-2013-0136773, 15 pages.
Rejection Decision dated May 21, 2020 in connection with Chinese Patent Application No. 201480061669.X, 31 pages.

* cited by examiner

METHOD AND APPARATUS FOR PROVIDING APPLICATION INFORMATION

CROSS-REFERENCE TO RELATED APPLICATION(S) AND CLAIM OF PRIORITY

The present application is related to and claims the benefit under 35 U.S.C. § 119(a) of a Korean patent application filed in the Korean Intellectual Property Office on Nov. 12, 2013 and assigned Serial No. 10-2013-0136773, the entire disclosure of which is hereby incorporated by reference.

TECHNICAL FIELD

The present disclosure relates to an electronic device, and more particularly, a method and apparatus for providing application information.

BACKGROUND

With the improvement of capability of an electronic device (e.g., a smart phone) or a wearable electronic device, the electronic device can provide a user with an application having various functions (e.g., measuring of a physical activity level or providing of a motion picture). For example, the electronic device can display a variety of information (e.g., the measured physical activity level or the executed motion picture) processed (or executed) by the application with respect to a user in a visual manner through a display operatively connected to the electronic device.

With the diversification of the function of the application, the electronic device can provide the user with various types of information related to the application according to a feature of the function provided by the application. For example, an application capable of measuring the physical activity level of the user on the based on motion of the user (hereinafter, for convenience of explanation, a health care application) can sense the motion of the user and can visually provide the user with information (e.g., speed information or information of a posture taken by the user) related to the sensed motion of the user. In addition, the health care application can provide the user with information on a physical activity level which varies depending on the motion of the user or information of calories burned depending on the motion.

The electronic device cannot provide the user with various types of information related to an application via one display, and provides only one important information. For example, in case of the health care application, the electronic device provides the user with only information related to the motion via one display, or provides only information related to the physical activity level. In this case, the user cannot simultaneously confirm information on the motion of the user and information on the physical activity level which varies depending on the motion. Thus, there is an inconvenience in the use of the application. In addition, if the user intends to confirm different information (e.g., the information related to the physical activity level) other than information currently being provided via the display (e.g., the information related to the motion), in order to acquire information to be confirmed, the user has to inconveniently perform a new input for changing the type of information provided by the electronic device.

SUMMARY

To address the above-discussed deficiencies, it is a primary object to provide a method and apparatus for providing application information capable of providing an improved user convenience when using an application, by simultaneously providing a variety of information related to the application (or a function of the application).

In accordance with the present disclosure, a method for providing application information is provided. The method includes providing at least one application item including information regarding a corresponding application, by using a first specified area of a display operatively coupled to an electronic device, identifying at least one item from the at least one application item, providing execution information of an application corresponding to the at least one item via a second specified area of the display based on the identifying, and providing additional information related to the execution information via the first specified area, based on the execution information.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely. Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

Figure 1:
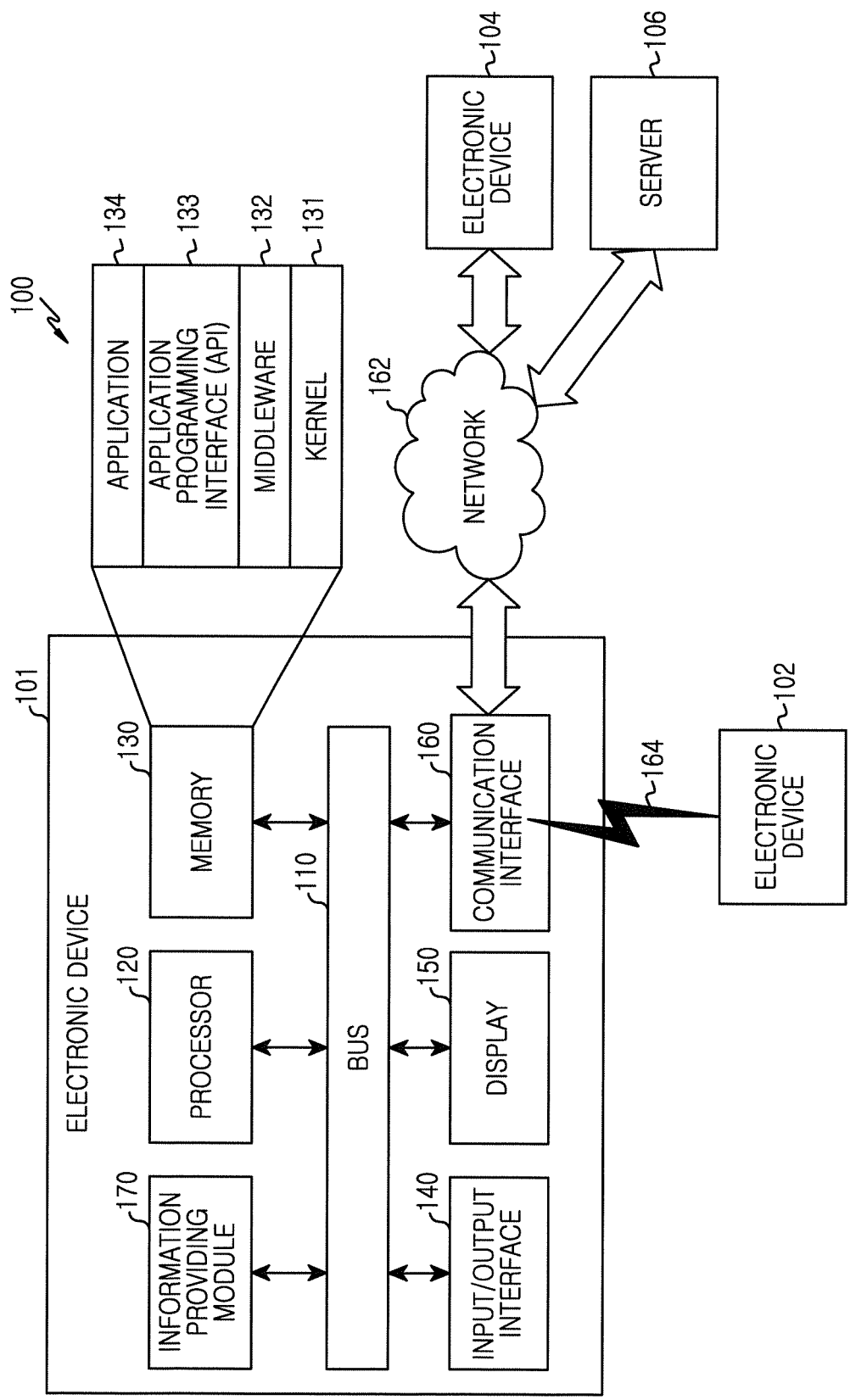
FIG. 1 illustrates a network environment including an electronic device according to various embodiments of the present disclosure.

FIGS. 1 through 9, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged wireless communication device. Hereinafter, the present disclosure is described with reference to the accompanying drawings. While the present disclosure is susceptible to various modifications and alternative forms, a specific embodiment thereof has been shown by way of example in the drawings and will herein be described in detail. It should be understood, however, that it is not intended to limit the present disclosure to the particular form disclosed, but, on the contrary, the present disclosure is to cover all modifications, equivalent, and alternatives falling within the spirit and scope of the present disclosure as defined by the appended claims. Like reference numerals denote like components throughout the drawings.

The expression "include" or "may include" used in the present disclosure is intended to indicate a presence of a corresponding function, operation, or component, and it is not intended to limit a presence of one or more functions, operations, or components. In addition, the term "include" or "have" is intended to indicate that characteristics, numbers, steps, operations, components, and elements disclosed in the specification or combinations thereof exist. As such, the term "include" or "have" should be understood that there are additional possibilities of one or more other characteristics, numbers, steps, operations, components, elements or combinations thereof.

In the present disclosure, an expression "or" includes any and all combinations of words enumerated together. For example, "A or B" may include A or B, or may include both A and B.

Although expressions such as "first", "second", "first", and "second" may be used to express various components of the present disclosure, it is not intended to limit the corresponding components. For example, the above expressions are not intended to limit an order or an importance of the corresponding components. The above expressions may be used to distinguish one component from another component. For example, a first user device and a second user device are both user devices, and indicate different user devices. For example, a first component may be termed a second component, and similarly, the second component may be termed the first component without departing from the scope of the present disclosure.

When a component is mentioned as being "connected" to or "accessing" another component, this may mean that it is directly connected to or accessing the other component, but it is to be understood that there are no intervening components present. On the other hand, when a component is mentioned as being "directly connected" to or "directly accessing" another component, it is to be understood that there are no intervening components present.

The terminology used in the present disclosure is for the purpose of describing particular embodiments only and is not intended to be limiting of the present disclosure. A singular expression includes a plural expression unless there is a contextually distinctive difference therebetween.

Unless otherwise defined, all terms (including technical and scientific terms) used herein have the same meaning as commonly understood by those ordinarily skilled in the art to which the present disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

An electronic device according to the present disclosure may be a device including a communication function. For example, the electronic device may include at least one of a smart phone, a tablet Personal Computer (PC), a mobile phone, a video phone, an e-book reader, a desktop PC, a laptop PC, a netbook computer, a Personal Digital Assistant (PDA), a Portable Multimedia Player (PMP), a MPEG-1 Audio Layer 3 (MP3) player, a mobile medical device, a camera, and a wearable device (e.g., a Head-Mounted-Device (HMD) such as electronic glasses, electronic clothes, an electronic bracelet, an electronic necklace, an electronic appcessory, an electronic tattoo, or a smart watch).

According to certain embodiments, the electronic device may be a smart white appliance having a communication function. For example, the smart white appliance may include at least one of a TeleVision (TV), a Digital Video Disk (DVD) player, an audio, a refrigerator, an air conditioner, a cleaner, an oven, a microwave oven, a washing machine, an air purifier, a set-top box, a TV box (e.g., Samsung HomeSync™, Apple TV™, or Google TV™), a game console, an electronic dictionary, an electronic key, a camcorder, and an electronic picture frame.

According to certain embodiments, the electronic device may include at least one of various medical devices (e.g., Magnetic Resonance Angiography (MRA), Magnetic Resonance Imaging (MRI), Computed Tomography (CT), imaging equipment, ultrasonic instrument, etc.), a navigation device, a Global Positioning System (GPS) receiver, an Event Data Recorder (EDR), a Flight Data Recorder (FDR), a car infotainment device, an electronic equipment for ship (e.g., a vessel navigation device, a gyro compass, etc.), avionics, a security device, and an industrial or domestic robot.

According to certain embodiments, the electronic device may include at least one of a furniture or a part of building/constructions including a communication function, an electronic board, an electronic signature input device, a projector, and various measurement machines (e.g., water supply, electricity, gas, propagation measurement machine, etc.). The electronic device according to the present disclosure may be one or more combinations of the aforementioned various devices. In addition, it is apparent those ordinarily skilled in the art that the electronic device according to the present disclosure is not limited to the aforementioned devices.

Hereinafter, an electronic device according to various embodiments of the present disclosure will be described with reference to the accompanying drawings. The term 'user' used in the various embodiments refers to a person who uses the electronic device or a device which uses the electronic device (e.g., an Artificial Intelligence (AI) electronic device). Hereinafter, more information related to a method and apparatus for providing application information according to the various embodiments is disclosed below in association with FIG. 1 to FIG. 9.

FIG. 1 illustrates a network environment 100 including an electronic device 101 according to various embodiments of the present disclosure. Referring to FIG. 1, the electronic device 101 may include a bus 110, a processor 120, a memory 130, an input/output interface 140, a display 150, a communication interface 160, and an information providing module 170.

The bus 110 may be a circuit for connecting the aforementioned components (e.g., the processor 120, the memory 130, the input/output interface 140, the display 150, the communication interface 160, or the information providing module 170) to each other and for delivering communication signals (e.g., a control message) between the aforementioned components.

The processor 120 may receive an instruction from the aforementioned different components (e.g., the memory 130, the input/output interface 140, the display 150, the communication interface 160, or the information providing module 170), for example, via the bus 110, and thus may interpret the received instruction and execute arithmetic or data processing according to the interpreted instruction.

The memory 130 may store an instruction or data received from the processor 120 or different components (e.g., the input/output interface 140, the display 150, the communication interface 160, or the information providing module 170) or generated by the processor 120 or the different components. The memory 130 may include programming modules such as a kernel 131, a middleware 132, an Application Programming Interface (API) 133, an application 134, and the like. Each of the aforementioned programming modules may consist of software, firmware, or hardware entities or may consist of at least two or more combinations thereof.

The kernel 131 may control or manage the remaining other programming modules, for example, system resources (e.g., the bus 110, the processor 120, the memory 130, etc.) used to execute an operation or function implemented in the middleware 132, the API 133, or the application 134. In addition, the kernel 131 may provide a controllable or manageable interface by accessing individual components of the electronic device 101 in the middleware 132, the API 133, or the application 134.

The middleware 132 may perform a mediation role so that the API 133 or the application 134 communicates with the kernel 131 to exchange data. In addition, regarding task requests received from the application 134, for example, the middleware 132 may perform a control (e.g., scheduling or load balancing) for the task requests by using a method of assigning a priority capable of using a system resource (e.g., the bus 110, the processor 120, the memory 130, etc.) of the electronic device 101 to at least one of the applications 134.

The API 133 may include at least one interface or function (e.g., instruction) for file control, window control, video processing, character control, and the like, as an interface capable of controlling a function provided by the application 134 in the kernel 131 or the middleware 132.

According to various embodiments of the present disclosure, the application 134 may include an Short Message Service (SMS)/Multimedia Messaging Service (MMS) application, an e-mail application, a calendar application, an alarm application, a health care application (e.g., an application for measuring a physical activity level, a blood sugar, etc.) or an environment information application (e.g., atmospheric pressure, humidity, or temperature information). Additionally or alternatively, the application 134 may be an application related to an information exchange between the electronic device 101 and an external electronic device (e.g., an electronic device 102 or an electronic device 104). The application related to the information exchange may include, for example, a notification relay application for relaying specific information to the external electronic device or a device management application for managing the external electronic device.

For example, the notification relay application may include a function of relaying notification information generated in another application (e.g., an SMS/MMS application, an e-mail application, a health care application, an environment information application, etc.) of the electronic device 101 to the external electronic device (e.g., the electronic device 102 or the electronic device 104). Additionally or alternatively, the notification relay application may receive notification information, for example, from the external electronic device (e.g., the electronic device 102 or the electronic device 104) and may provide it to the user. The device management application may manage, for example, a function for at least one part of the external electronic device (e.g., the electronic device 102 or the electronic device 104) which communicates with the electronic device 101. Examples of the function include turning on/turning off the external electronic device itself (or some components thereof) or adjusting of a display illumination (or a resolution), and managing (e.g., installing, deleting, or updating) of an application which operates in the external electronic device or a service (e.g., a call service or a message service) provided by the external electronic device.

According to various embodiments of the present disclosure, the application 134 may include an application specified according to attribute information (e.g., an electronic device type) of the external electronic device (e.g., the electronic device 102 or the electronic device 104). For example, if the external electronic device is an MP3 player, the application 134 may include an application related to a music play. Similarly, if the external electronic device is a mobile medical device, the application 134 may include an application related to a health care. The application 134 may include at least one of a specified application in the electronic device 101 or an application received from the external electronic device (e.g., a server 106, the electronic device 102, or the electronic device 104).

The input/output interface 140 may relay an instruction or data input from a user by using a sensor (e.g., an acceleration sensor, a gyro sensor) or an input device (e.g., a keyboard or a touch screen) to the processor 120, the memory 130, the communication interface 160, or the information providing module 170, for example, via the bus 110. For example, the input/output interface 140 may provide data regarding a user's touch input via the touch screen to the processor 120. In addition, the input/output interface 140 may output an instruction or data received from the processor 120, the memory 130, the communication interface 160, or the information providing module 170 to an output device (e.g., a speaker or a display), for example, via the bus 110. For example, the input/output interface 140 may output audio data provided by using the processor 120 to the user via the speaker.

The display 150 may display a variety of information (e.g., multimedia data or text data) to the user.

The communication interface 160 may connect a communication between the electronic device 101 and an external device (e.g., the electronic device 102, the electronic device 104, or the server 106). For example, the communication interface 160 may support a network communication 162 (e.g., Internet, Local Area Network (LAN), Wide Area Network (WAN), telecommunication network, cellular network, satellite network, Plain Old Telephone Service (POTS), etc.) and a short range communication 164 (e.g., Wireless Fidelity (Wi-Fi), Bluetooth (BT), Near Field Communication (NFC), or wired communication (e.g., Universal Serial Bus (USB), High Definition Multimedia Interface (HDMI), Recommended Standard (RS)-232, POTS, etc.). A protocol for a communication between the electronic device 101 and the external device (e.g., a short range communication protocol, a network communication protocol, or a wired communication protocol) may be supported in at least one of the API 133 and the middleware 132. Each of the electronic devices 102 and 104 may be a device which is the same (e.g., the same type) as the electronic device 101 or may be a different (e.g., a different type) device.

The information providing module 170 may process at least a portion of information acquired from different components (e.g., the processor 120, the memory 130, the input/output interface 140, or the communication interface 160), and may provide this to the user in various manners. For example, the information providing module 170 may control the display 150 to provide information related to at least a portion of the application 134 by the use of the processor or, independently thereof, by the use of the display 150. In certain embodiments, the information providing module 170 may be included in the processor 120 or the memory 130 or may be an independent module. More information on the information providing module 170 is provided by reference to FIG. 2 to FIG. 8 described below.

Figure 2:
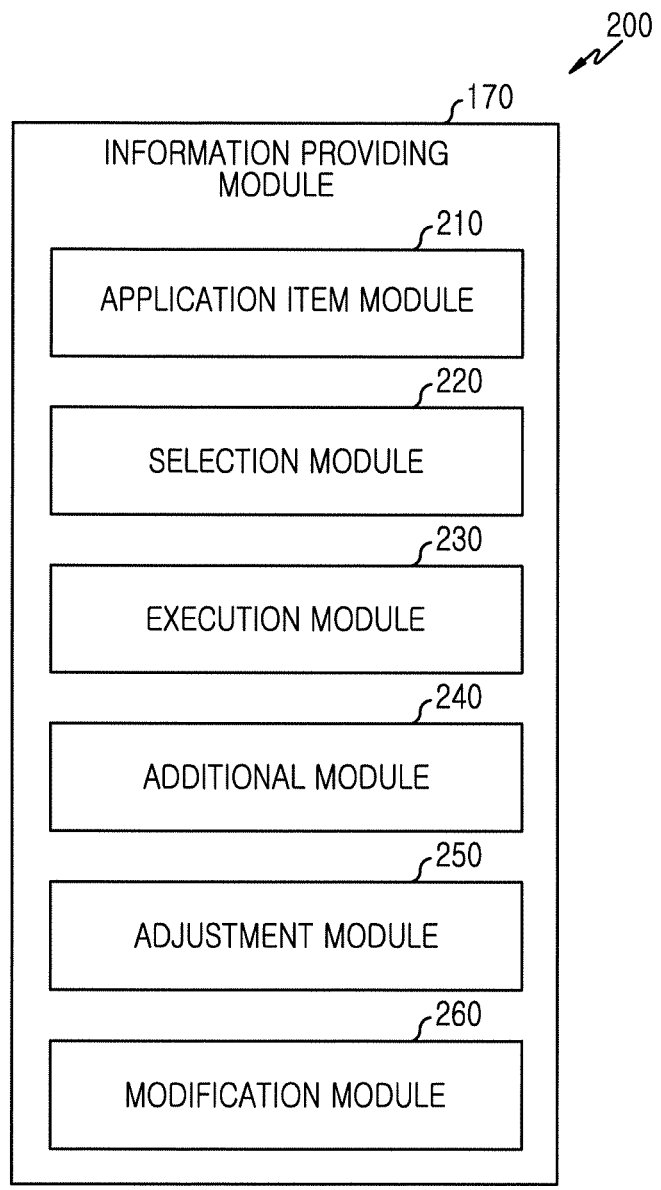
FIG. 2 illustrates a block diagram of an information providing module according to various embodiments of the present disclosure.

FIG. 2 illustrates a block diagram 200 for the information providing module 170 according to various embodiments of the present disclosure. Referring to FIG. 2, the information providing module 170 may include, for example, an application item module 210, a selection module 220, an execution module 230, an additional module 240, an adjustment module 250, and a modification module 260. For example, the application item module 210 may generate at least one application item that can be displayed to a display (e.g., the display 150). Each of the at least one application item may include information for a corresponding application.

For example, an Internet application, a phone application, a navigation application, or a health care application may be executed by using the electronic device (e.g., the electronic device 101). In this case, the application item module 210 may generate at least one of an Internal application item corresponding to the Internal application, a phone application item corresponding to the phone application, a navigation application item corresponding to the navigation application, or a health care application item corresponding to the health care application.

The application item module 210 may provide at least one application item to the display, so that the display (e.g., the display 150) can display at least one application item to a user. The application item module 210 controls the display such that at least one application item can be provided to the user by using a specified area of the display (hereinafter, for convenience of explanation, an additional area).

For example, the application item may be expressed with at least one of an image, text, or combination thereof related to a corresponding application. In addition, the application item may be a selection menu provided to the user enabling the user to select an application to be executed by using the electronic device (e.g., the electronic device 101).

The selection module 220 may select at least a portion of an application to be executed by the electronic device in the at least one application item. The selection module 220 may select the application item based on a user input. For example, the selection module 220 may acquire a user input (e.g., a touch input or a hovering input) for selecting the application item by using a device (e.g., a touch screen) operatively coupled to the display.

In addition, the selection module 220 may determine an area in which the user input (e.g., the touch input or the hovering input) is acquired, and may confirm to which application item the area is related in the at least one application item. For example, the selection module 220 may determine a touch input sensed in at least a portion of an area in which the application item is displayed, as a user input for selecting the application item. In addition, the selection module 220 may determine, for example, a user input for dragging an application item selected by a touch input to a specified area, as the user input for selecting the application item.

In the aforementioned example, for convenience of explanation, a method of acquiring a user input by the selection module 220 by using a touch screen is described. However, according to certain embodiments, the selection module 220 may acquire a user input for selecting an application item by using a hovering input based on an electronic pen, a sound input, a button input, or a combination thereof. More information for the method of acquiring the user input by the selection module 220 is described below, for example, with reference to FIG. 3.

The selection module 220 may select an application item based on a situation related to the electronic device. For example, the selection module 220 may select the application item based on location information of the electronic device. The selection module 220 may acquire the location information of the electronic device based on information acquired by using a location detection module (e.g., a GPS or a short range communication module (e.g., Wi-Fi or BT)) operatively coupled to the selection module 220. The selection module 220 may confirm (or select) a specified application item according to the location information of the electronic device. In this case, an application corresponding to the specified application item according to the location information of the electronic device may be executed by using the electronic device.

For example, if it is determined that the electronic device is located inside a car, the selection module 220 may select an application item corresponding to a music play application specified in location information indicating "inside a car" in the at least one application. In addition, if it is determined that the electronic device is located in an office, the selection module 220 may select an application item corresponding to a schedule application specified in location information indicating "an office" in the at least one application item. Situation information of the electronic device may include, for example, not only the location information of the electronic device but also communication information (e.g., Wi-Fi, BT, NFC, etc.), battery information, motion information, and the like of the electronic device.

The electronic device (e.g., the electronic device 101) may further include a memory (e.g., the memory 130) capable of storing situation information of the electronic device and information for an application item corresponding to the situation information of the electronic device. In this case, the selection module 220 may select an application item corresponding to the situation information of the electronic device, based on the information stored in the memory (namely, the situation information of the electronic device and the information on the application item).

The selection module 220 may select an application item based on attribute information related to an application. For example, an environment information application may be executed by using the electronic device (e.g., the electronic device 101). The environment information application may provide the user with information regarding, for example, at least one of a temperature, humidity, and illumination of a surrounding environment for the electronic device. In this case, attribute information of the environment information application may be information regarding, for example, at least one of a temperature, humidity, illumination, and air quality of the surrounding environment.

The selection module 220 may select an application item corresponding to an application (e.g., a temperature adjustment application) capable of controlling a temperature of the surrounding environment, based on temperature information which is one of attribute information of the environment information application. For example, the selection module 220 may acquire the temperature information of the surrounding environment of the electronic device, by using a temperature sensor operatively coupled to the electronic device. The selection module 220 may determine whether an ambient temperature is included in a specified pleasant temperature range (e.g., 20 to 26° C.). If the ambient temperature is not included in the specified pleasant temperate range, the selection module 220 may select an application item (e.g., a temperature adjustment application item) corresponding to an application capable of adjusting the ambient temperature.

For example, a health care application may be executed by using the electronic device (e.g. the electronic device 101). Attribute information of the health care application may include, for example, a physical activity level (e.g., pace counter information), food intake information, and the like of the user. The selection module 220 may compare the user's physical activity level provided by using the health care application with a daily appropriate physical activity level (e.g., 250 to 300 calories). If the current user's physical activity level is less than the daily appropriate physical activity level, the selection module 220 may select an application item corresponding to a fitness equipment to execute an application capable of the providing instructions associated with the fitness equipment.

The execution module 230 may execute an application corresponding to an application item selected by using the selection module 220. In addition, the execution module 230 may generate at least one execution information (e.g., information regarding a result of executing the application) corresponding to the application to be executed. The execution information may be, for example, a User Interface (UI) provided by using the display. For example, if the selection module 220 selects an application item related to a music play application, the execution module 230 may execute the music play application. In this case, the execution module 230 is execution information for the music play application, and may generate music title information, lyrics information, album information, or music list information corresponding to a UI of the music play application.

The execution module 230 may provide at least one execution information to the display, so that the display (e.g., the display 150) can display at least one execution information of an application which is currently being executed for the user. In addition, the execution module 230 may control the display such that the at least one execution information can be displayed by using a specified area of the display (hereinafter, for convenience of explanation, an execution area). The execution area in which the execution information is displayed may be a different area distinguished from the additional area.

The additional module 240 may generate additional information related to the execution information based on the execution information. For example, the additional information may include a control menu capable of acquiring a user input to control at least one function of an application being executed in the electronic device. In addition, the additional information may include information corresponding to at least one of a function for the application being executed in the electronic device and a function for an application different from the previous application. More information on the additional information is described below in association with FIG. 7A and FIG. 7B.

The additional module 240 may provide at least one additional information to the display, so that the display (e.g., the display 150) can display the at least one additional information to the user. In addition, the additional module 240 may control the display such that the at least one additional information is displayed by using an additional area which is a specified area of the display. For example, the additional module 240 may control the display such that the additional information is displayed by using at least a portion of the additional area, based on a fact that the execution information is displayed in the execution area. The additional module 240 may control the display such that the additional information is displayed during the execution information is displayed via the display.

The additional module 204 may determine an attribute (e.g., at least one of a location, a size, a shape, and a color) of at least a portion of an area for providing the additional information in the additional area. More information regarding the method of determining an attribute of the least the portion of the area is described below in association with FIG. 4.

The adjustment module 250 may control the display to output by adjusting an attribute (e.g., at least one of a location, a size, a shape, and a color) of the execution area or the additional area. The adjustment module 250 may adjust at least one of the location, the size, the shape, and the color of the additional area or the execution area based on at least one of situation information related to the electronic device or the application, attribute information of the additional information or the execution information, or user's state information. More information regarding a method of adjusting the attribute of the execution area or the additional area is described below, for example, in association with FIG. 5 and FIG. 6.

The adjustment module 250 may control the display or an input device (e.g., a touch screen) operatively coupled to the electronic device so that the execution area or the additional area is selectively activated or deactivated. For example, the adjustment module 250 may control the input device (e.g., the touch screen) operatively coupled to the electronic device so that a user input (e.g., an input for touching at least a portion of the execution area or the additional area) related to the execution area or the additional area is acquired in a distinctive manner. For example, the adjustment module 260 may control the input device such that the electronic device acquires only the user input related to at least one of the execution area or the additional area. More information regarding a method of controlling the input device is described below, for example, in association with FIG. 7C.

The modification module 260 may modify the execution information or the additional information. For example, the modification module 260 may generate modified execution information according to at least one of a user input related to the execution information, situation information related to the electronic device (e.g., the electronic device 101), or attributed information related to an application executed in the electronic device, and user's state information. In this case, the modification module 260 may generate the modified additional information, based on the modified execution information.

For example, if a music play application is executed in the electronic device (e.g., the electronic device 101), the electronic device (e.g., the information providing module 170) may provide a music play list as the execution information, and may provide a control menu (e.g., a menu for moving to a previous song, a menu for moving to a next song) capable of controlling the music play list, as the additional information. If a music to be played back in the electronic device is selected from the music play list by a user input (e.g., a touch or hovering input), the modification module 260 may generate information (e.g., a music title, a singer's name) on the selected music as the modified execution information. In addition, the modification module 260 may generate a control menu (e.g., a volume control menu, a music pause menu) for controlling the music selected according to the modified execution information as the modified additional information.

For example, if an environment information application is executed in the electronic device, the electronic device (e.g., the information providing module 170) may provide current temperature information as the execution information, and may provide a pleasant level of a current temperature as the additional information. In this case, attribute information of the environment information application may be temperature information of a surrounding environment. The modification module 260 may generate temperature information modified based on the temperature change of the surrounding environment as the modified execution information. In addition, the modification module 260 may generate modified pleasant level information as the modified additional information, based on the modified execution information.

For example, if a health care application is executed in the electronic device, the electronic device (e.g., the information providing module 170) may provide physical activity level information (e.g., walking information) as the execution information, and may provide calorie burn information related to the physical activity level information as the additional information. The modification information 260 may generate physical activity level information modified based on a user's movement (e.g., a change in a user's state) as the modified execution information. In addition, the modification module 260 may generate calorie burn information modified based on the modified execution information as the modified additional information. More information related to a method of generating the execution information modified based on situation information related to the electronic device is described below, for example, in association with FIG. 7D.

The modification module 260 may generate modified additional information according to at least one of a user input related to the additional information, situation information related to the electronic device of the additional information, and a change in a user's state. In this case, the modification module 260 may generate the modified execution information based on the modified additional information.

For example, if a navigation application is executed in the electronic device (e.g., the electronic device 101), the electronic device (e.g., the information providing module 170) may provide map information as the execution information, and may provide compass information (e.g., direction information) as the additional information. The modification module 260 may generate modified compass information as the modified additional information according to a rotation (e.g., situation information related to the electronic device) of the electronic device (e.g., the electronic device 101). In addition, the modification module 260 may generate new information (e.g., region information corresponding to the direction) related to the modified compass information as the modified execution information.

For example, if a health care application is executed in the electronic device, the electronic device (e.g., the information providing module 170) may provide physical activity level information as the additional information, and may provide evaluation information for evaluating a user's physical activity level (e.g., a goal achievement, an insufficient physical activity, etc.) as the execution information. The modification module 260 may generate physical activity level information that is modified based on a change in a user's physical activity level (e.g., a change in a user's state) as the modified additional information. In addition, the modification module 260 may generate evaluation information modified based on the modified additional information as the modified execution information. A method of generating the additional information modified based on the situation information related to the user input or the additional information is described below, for example, in association with FIG. 7E.

The modification module 260 may provide the modified execution information or the modified additional information to the display (e.g., the display 150). In addition, the modification module 240 may control the display such that the modified execution information or the modified additional information is displayed via the display. In this case, the modification module 240 may control the display such that the modified execution information is displayed in an area (e.g., located on an adjacent or parallel line) related to an area in which the modified additional information is displayed. More information related to a method of configuring the area in which the modified execution information is displayed is described below, for example, in association with FIG. 7E.

Figure 3:
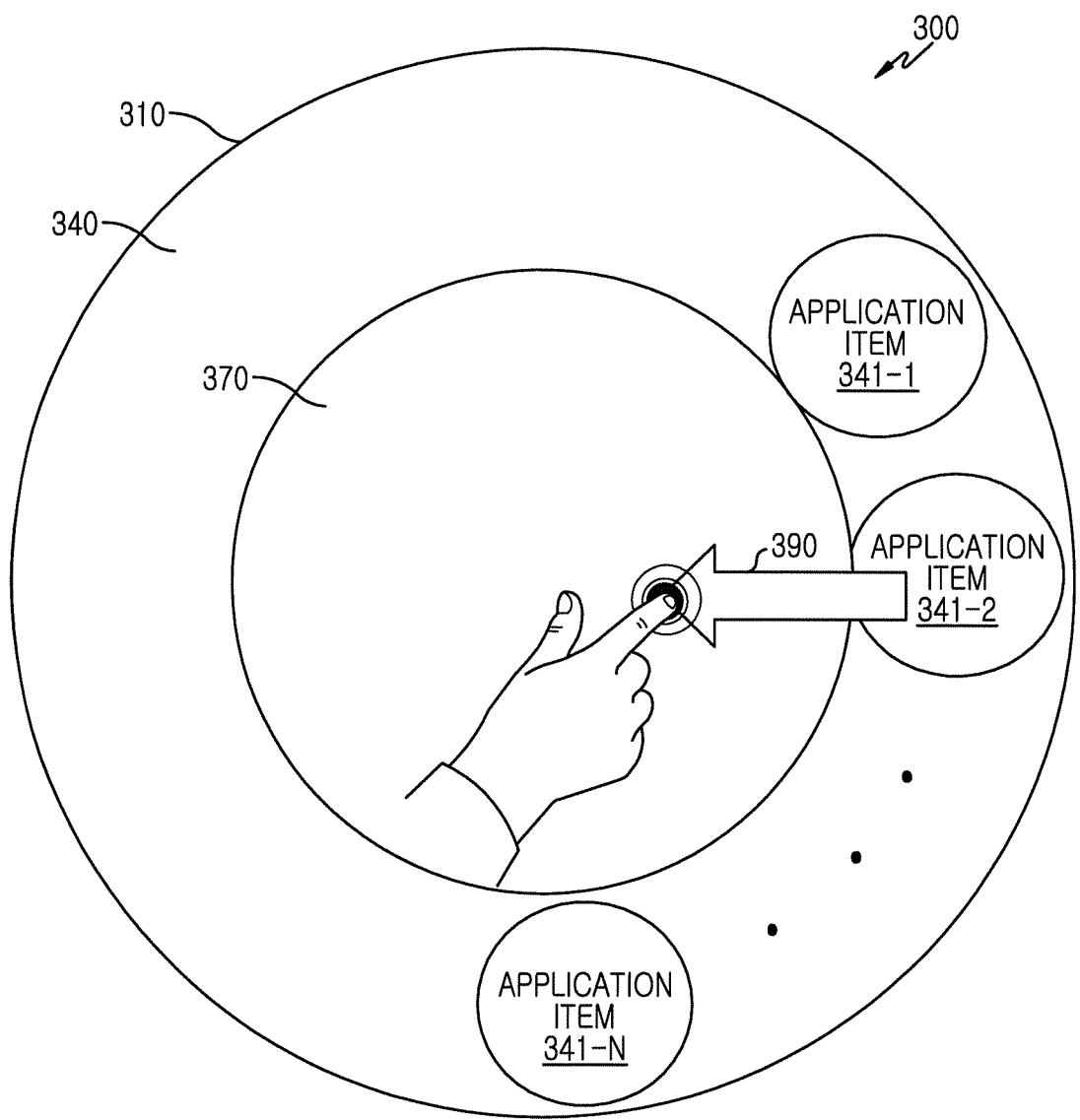
FIG. 3 illustrates an example of applying a User Interface (UI) for providing application information in an electronic device according to various embodiments of the present disclosure.

FIG. 3 illustrates an example 300 of applying a UI for providing an application item by using a display 310 (e.g., the display 150) in an electronic device (e.g., the information providing module 170) according to various embodiments of the present disclosure. Referring to FIG. 3, the display 310 may have a circular shape for example. According to a certain embodiments, the shape of the display (e.g., the display 310) may be not only circular in shape but also various shapes such as a square, a rectangle, a triangle, and the like.

The display 310 may include an additional area 340 which displays (or will display) application items 341-1 to 341-N in a visual manner to the user and an execution area 370 which displays (or will display) execution information of an application in a visual manner. Each of the application items 341-1 to 341-N may be, for example, information consisting of an image (e.g., an icon or a photo) or a text (e.g., a link) or a combination thereof for a corresponding application. The additional area 340 and the execution area 370 may be an area separated in a hardware or software manner. For example, the additional area 340 and the execution area 370 may be configured respectively in different displays which are physically distinctive. Alternatively, the additional area 340 and the execution area 370 may be configured physically in one display, but may be distinctive in a software manner.

For example, as illustrated in FIG. 3, the additional area 340 may be located in at least a portion of a peripheral area of the display 310, and the execution area 370 may be located in at least a portion of an area surrounded at least partially by the additional area 340. According to a certain embodiments, the additional area 340 may be located in at least a portion of an upper side of the display 310, and the execution area 370 may be located in at least a portion of a lower side of the display 310 (the other way around is also possible). The additional area 340 may be located in at least a portion of a left side of the display 310, and the execution area 370 may be located in at least a portion of a right side of the display 310 (the other way around is also possible). The additional area 340 and the execution area 370 may be located in another area (e.g., a left-lower portion or a right-upper portion) of the display 310 (the other way around is also possible).

According to the present example 300, the electronic device the selection module 220) may touch an application item 341-2, and may select the application item 341-2 among the application items 341-1 to 341-N, based on a user input 390 for dragging the touched application item 341-2 to the execution area 370. As illustrated in FIG. 3, the plurality of application items 341-1 to 341-N may be displayed in the additional are 340 of the display 310. In addition, the application item 341-2 may be selected from the application items 341-1 to 341-N provided to the additional area 340 according to the user input 390.

For example, the user input 390 may be an input for touching (or hovering) the application item 341-2, as an input acquired from an area (e.g., at least a portion of an area in which the application item 341-2 is displayed) corresponding to the application item 341-2. In addition, the user input 390 may be, for example, an input for moving the application item 341-2 from the additional area 340 to the execution area 370. According to the user input 390, an application corresponding to the application item 341-2 may be executed via the electronic device.

Figure 4:
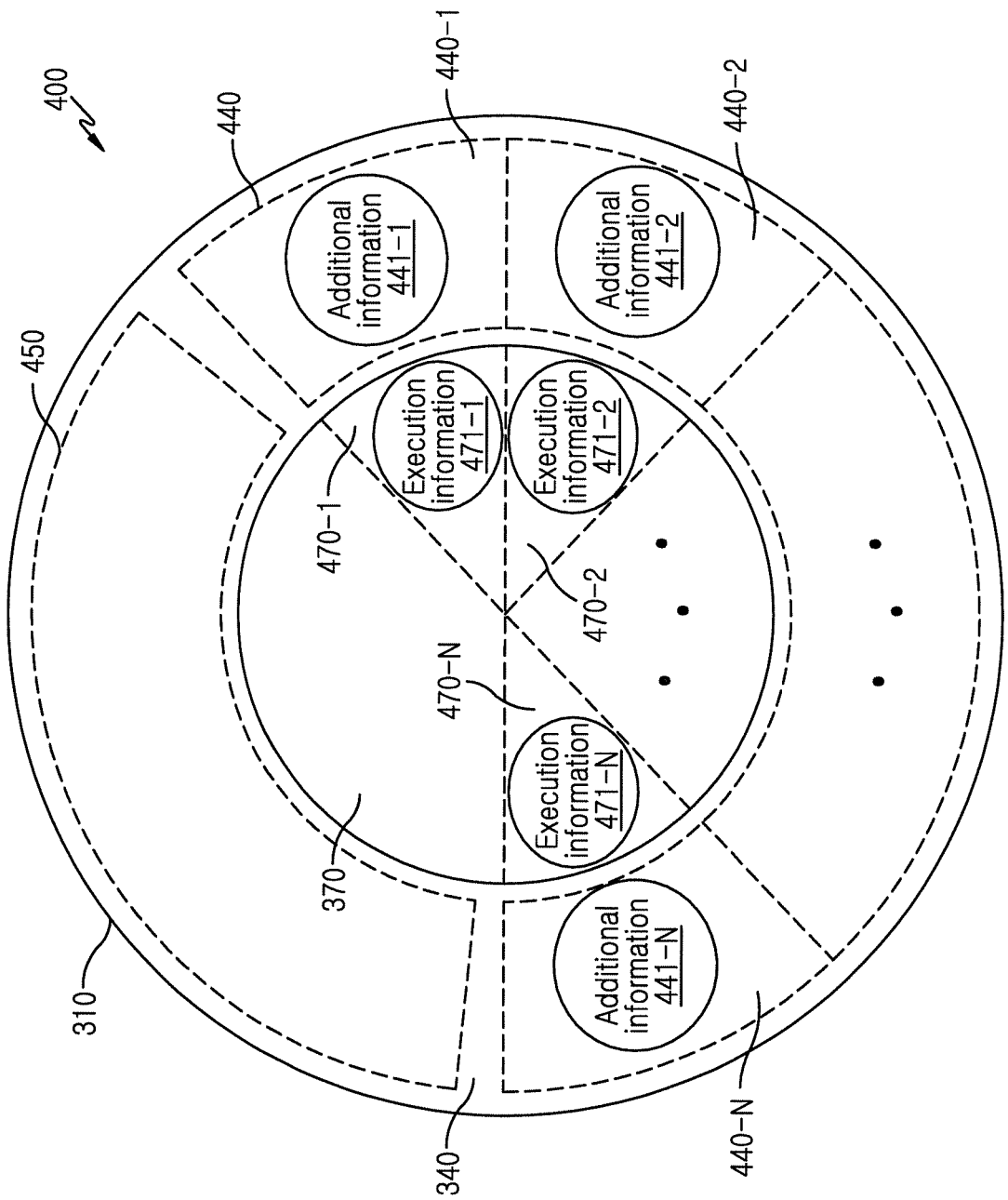
FIG. 4 illustrates an example of applying a UI for providing application information in an electronic device according to various embodiments of the present disclosure.

FIG. 4 illustrates an example 400 of applying a UI for providing application information via the display 310 (e.g., the display 150) in an electronic device (e.g., the information providing module 170) according to various embodiments of the present disclosure. According to the example 400, if an application item (e.g., the application item 341-2) is selected from application items (e.g., the application items 341-1 to 341-N), application execution information 471-1 to 471-N corresponding to the application item (e.g., the application item 341-2) may be displayed in the execution area 370. In addition, at least one or more additional information 441-1 to 441-N related to the execution information 471-1 to 471-N may be displayed in the additional area 340.

The execution information 471-1 to 471-N may be displayed in the execution area 370 in a distinctive manner. For example, the execution information 471-1 may be displayed in a sub-area 470-1 of the execution area 370, the execution information 471-2 may be displayed in a sub-area 470-2 of the execution area 370, and the execution information 471-N may be displayed in a sub-area 470-N of the execution area 370. The sub-areas 470-1 to 470-N respectively corresponding to the execution information 471-1 to 471-N may partially overlap with each other or may have a specified interval or may be in contact with each other.

Additional information 441-1 to 441-N corresponding the execution information 471-1 to 471-N may be displayed in the additional area 340. In certain embodiments, at least one of a location, size, shape, and color of the area 440 in which the additional information 441-1 to 441-N is displayed may be determined (e.g., modified), based on the execution information 471-1 to 470-N. For example, the additional information 441-1 to 441-N may be displayed at least in a sub-area of the additional area 340, based on an area in which the execution information 471-1 to 471-N is displayed.

Referring to FIG. 4, the additional information 441-1 (e.g., additional information for adjusting the execution information 471-1) corresponding to the execution information 471-1 may be output to an area 440-1 (e.g., located in an area partially in contact with the area 470-1) corresponding to the area 470-1 in which the execution information 471-1 is displayed. In addition, the additional information 441-2 (e.g., additional information for adjusting the execution information 471-2) corresponding to the execution information 471-2 may be output to an area 440-2 (e.g., located in an area partially in contact with the area 470-2) corresponding to the area 470-2 in which the execution information 471-2 is displayed. Similarly, the additional information 441-N (e.g., additional information for adjusting the execution information 471-N) corresponding to the execution information 471-N may be output to an area 440-N (e.g., located in an area partially in contact with the area 470-N) corresponding to the area 470-N in which the execution information 471-N is displayed. The area 470-1 in which the execution information 471-1 is displayed and the area 440-1 in which the additional information 441-1 corresponding to the execution information 471-1 is displayed may be displayed on the same parallel line.

For example, if a music play application is executed in the electronic device, execution information (e.g., volume information, lyrics information, or currently played duration information) corresponding to the music play application may be displayed in the execution area 370. If the volume information (e.g., the execution information 471-1) is displayed in a sub-area (e.g., an area 470-1) of the execution area 370, a control menu (e.g., the additional information 441-1) for controlling a volume of a music player may be displayed by using an area (e.g., the sub-area 440-1 of the additional area 340) corresponding to the volume information.

Although not shown, if a size of the area 470-1 in which the execution information 471-1 is displayed is greater than a size of an area 470-2 in which the execution information 471-2 is displayed, the additional information 441-1 corresponding to the execution information 471-1 may be output to an area wider than that of the additional information 441-2 corresponding to the execution information 471-2. For example, the area 440-N in which the additional information 441-N corresponding to the execution information 471-N is output (or to be output) may be output in a shape (e.g., the same shape as the area 470-N) related to the shape of the area 470-N in which the execution information 471-N is displayed. As another example, the area 440-1 in which the additional information 441-1 corresponding to the execution information 471-1 is displayed may be output with a color (e.g., the same color as the area 470-1) related to a color of the area 470-1 in which the execution information 471-1 is displayed.

An area in which a selected application item (hereinafter, for convenience of explanation, a "selection application item") is displayed may be an area in which additional information related to execution information of an application corresponding to the selection application item is displayed. For example, if the selection application item (e.g., the application item 341-2) is previously displayed in the sub-area 440-1 of the additional area 340, additional information related to the application corresponding to the selection application item may be displayed in the area 440-1.

Additional information regarding a currently not-selected different application item or an application (e.g., a next selectable application) corresponding to the currently not-selected application item may be displayed in an area 450 (hereinafter, for convenience of explanation, a "non-display area"). In non-display area 450, the additional information 441-1 to 441-N related to the currently executed application in the additional area 340 is not displayed.

For example, the application items may include a first application item and a second application item. If the first application item is selected, additional information related to execution information for the first application may be displayed in the sub-area 440 of the additional area 340. Additionally or alternatively, although not shown, the second application item may be displayed in a non-display area 450 of the additional area 340.

If the second application item is selected in a state where the execution of the first application is not complete, the first application and the second application may be both executed in the electronic device (e.g., the electronic device 101). In this case, additional information related to the execution information of the first application may be maintained and displayed in the sub-area 440 of the additional area 340, and additional information related to execution information of the second application may be displayed in the sub-area 450 (e.g., the non-display area 450) of the additional area 340. For example, if the first application and the second application are simultaneously executed, each corresponding execution information may be displayed simultaneously, alternatively, or sequentially in the execution area 370.

The application items may include the first application item displayed in the sub-area 440-1 of the additional area 340 and the second application item displayed in the sub-area 440-2 of the additional area 340. For example, although not shown, additional information related to execution information of the first application may be displayed in the sub-area 440-1, and the second application item may be displayed in the sub-area 440-2 by being maintained in the sub-area 440-2 in which the second application item is originally displayed.

Figure 5:
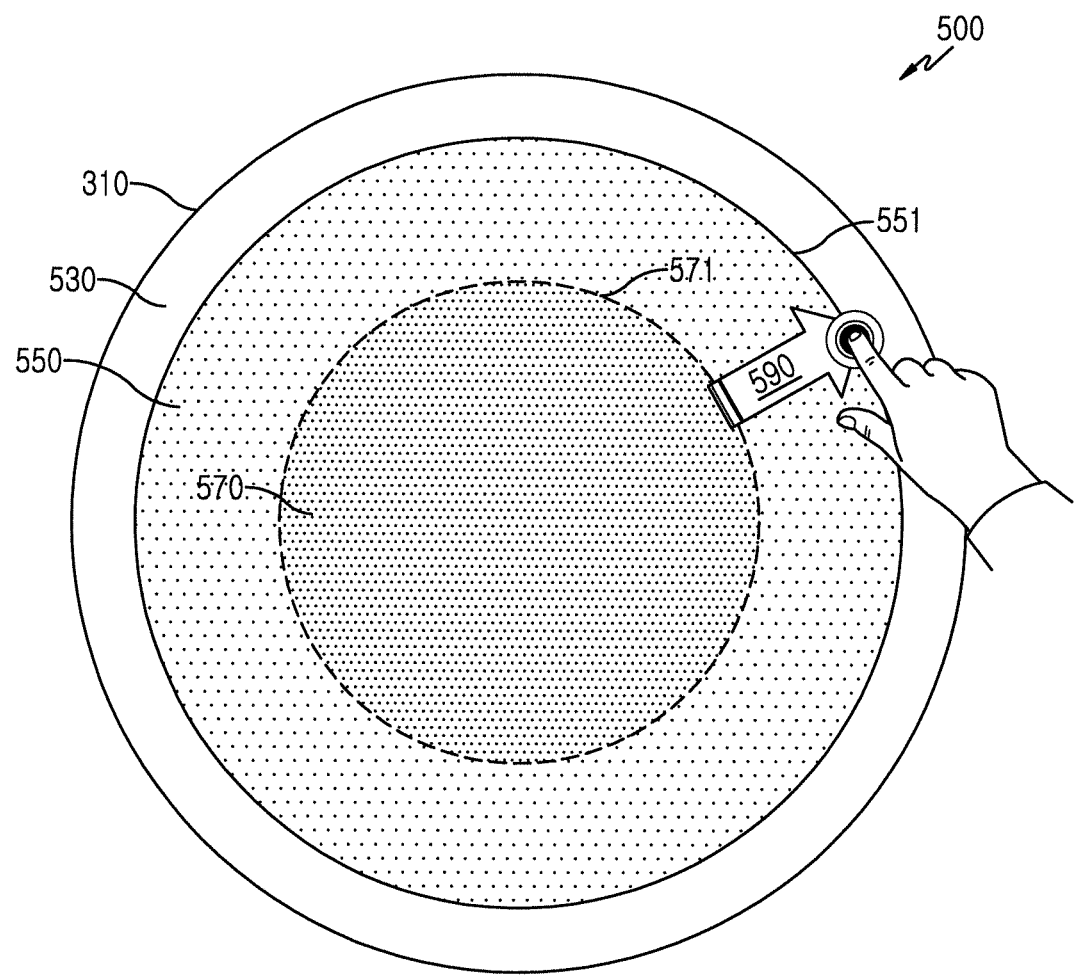
FIG. 5 illustrates an example of applying a UI for providing application information in an electronic device according to various embodiments of the present disclosure.

FIG. 5 illustrates an example 500 of applying a UI for providing application information to the display 310 (e.g., the display 150) by using an electronic device (e.g., the information providing module 170) according to various embodiments of the present disclosure. In FIG. 5, for convenience of explanation, it is shown that the display 310 is divided into a first area 530, a second area 550, and a third area 570. According to the example 500, an additional area (e.g., the additional area 340) and an execution area (e.g., the execution area 370) may be adjusted in size by using the electronic device (e.g., the adjustment module 250), based on a user input 590. For example, the size of the additional area may be decreased according to the user input 590, and the size of the execution area may be increased. In addition, the size of the additional area may be increased by the user input 590, and the size of the execution area may be decreased. For example, at least one of a location, shape, and color of the additional area (e.g., the additional area 340) and the execution area (e.g., the execution area 370) may be adjusted by using the electronic device (e.g., the adjustment module 250), based on the user input 590.

Referring to FIG. 5, in the absence of the user input 590, for example, an execution area before being modified (hereinafter, for convenience of explanation, a current execution area) may include only the third area 570, and an additional area before being modified (hereinafter, for convenience of explanation, a current additional area) may include the first area 530 and the second area 550. To modify a size of the current execution area (e.g., the third area 570), the user input 590 may touch a boundary 571 of the current execution area.

In addition, the user input 590 may drag the touched boundary 571 up to a boundary 551 (e.g., a boundary of the second area 550) of an execution area desired by a user (e.g., an area including the second area 550 and the third area 570, hereinafter, for convenience of explanation, a modified execution area). In this case, a size of the current execution area (e.g., the third area 570) provided to the user may be increased to a size of the modified execution area including the second area 550 and the third area 570. Since the execution area is increased from the current execution area including only the third area 570 to the area including the third area 570 and the second area 550, an additional area may be decreased from a current additional area including the first area 530 and the second area 550 to an area including only the first area 530.

Although not shown, a location of the execution area may be moved, for example, to the right based on the user input (e.g., the user input 590). According to one exemplary embodiment, based on the user input (e.g., the user input 590), a color of the execution area or the additional area may be selected, and the execution area or the additional area may be modified to the selected color. For example, based on the user input (e.g., the user input 590), a shape of the execution area or the additional area may be selected, and the execution area or the additional area may be modified to the selected shape.

For example, at least one of location, size, shape, and color information of the additional area and the execution area may be adjusted based on at least one of situation information related to the electronic device, attribute information related to an application, attribute information of additional information or execution information, and user's state information. For example, the location of the execution area may be moved (e.g., in an up, down, left, or right direction), based on a movement of the electronic device (e.g., a change in an inclination of the electronic device) as a situation information of the electronic device. In this case, the additional area may change in its location to the remaining areas not overlapping with the execution area in the display. In addition, if motion information of the electronic device as a situation information of the electronic device corresponds to a specified motion (e.g., a rotation about a vertical axis of the electronic device), the execution area may first include only the third area 570 and then may be extended to include the second area 550 and the third area 570. Since the execution area is extended to be wider along with an increase in a rotation speed of the electronic device, a user's visibility may be improved.

For example, if an ambient illumination of the electronic device as a situation information related to the electronic device corresponds to a specified range (e.g., a dark environment (i.e., about 10 lux)), at least one of colors of the execution area or the additional area may be modified to have a value brighter than a specified value. In addition, at least one of the execution area and the additional area may be expressed in various shapes specified based on various situation information of the electronic device. For example, if the execution information provides a content of a mail application, the execution area may be modified from a current shape (e.g., a circular shape) to a heart shape and the like.

Attribute information related to an application may include, for example, an amount of execution information related to the application. For example, if the amount of the execution information related to the application is great, a size of the execution area may be increased.

Attribute information of the additional information or the execution information may include an amount or type (e.g., a still image type, a moving image type, a text type, etc.) of the additional information or execution information. For example, if the number of pieces of additional information is great, the size of the additional area may first include only the first area 530 and then may be extended to include both of the second area 550 and the third area 570. In addition, if the type of the execution information is an image, the size of the execution area may be increased for an image readability in comparison with a case where the type of the execution information is a text.

The user's state information may include a proximity status (e.g., distance information) of the electronic device (e.g., the electronic device 101) and the user. For example, if a hand of the user is proximate to the additional area (e.g., a distance between the additional area and the hand is within 30 mm), the additional area may first include only the first area 530 and then may be extended to include the second area 550 and the third area 570, so that the user can easily touch the additional information. If the hand of the user is proximate to the execution area, the execution area may first include only the third area 570 and then may be extended to include the second area 550 and the third area 570.

If the execution area (e.g., the execution area 370) is extended by a size of the display 310, only the execution information of the application may be provided to the display 310 by using the electronic device (e.g., the information providing module 170). In addition, if the additional area (e.g., the additional area 340) is increased by the size of the display 310, only the additional information may be provided to the display 310 by using the electronic device (e.g., the information providing module 170). For example, the execution area or additional area of the display 310 may be displayed with a specified size by using the electronic device (e.g., the adjustment module 250).

For example, if the execution area is increased by the size of the display 310, the additional area may be increased to a specified size (e.g., a size of the first area 530) based on a user input (e.g., a touch or hovering input) for displaying the additional information, or the execution area may be displayed by being decreased to a specified size (e.g., a size of the third area 570). Similarly, if the additional area is increased by the size of the display 310, the execution area may be increased to a specified size (e.g., a size of the third area 570) based on a user input (e.g., a touch or hovering input) for displaying the execution information, or the additional area may be displayed by being decreased to a specified size (e.g., a size of the first area 530). The specified size may be, for example, a size specified according to at least one of situation information of an application, attribute information of additional information, a user configuration, and a combination of them.

Figure 6:
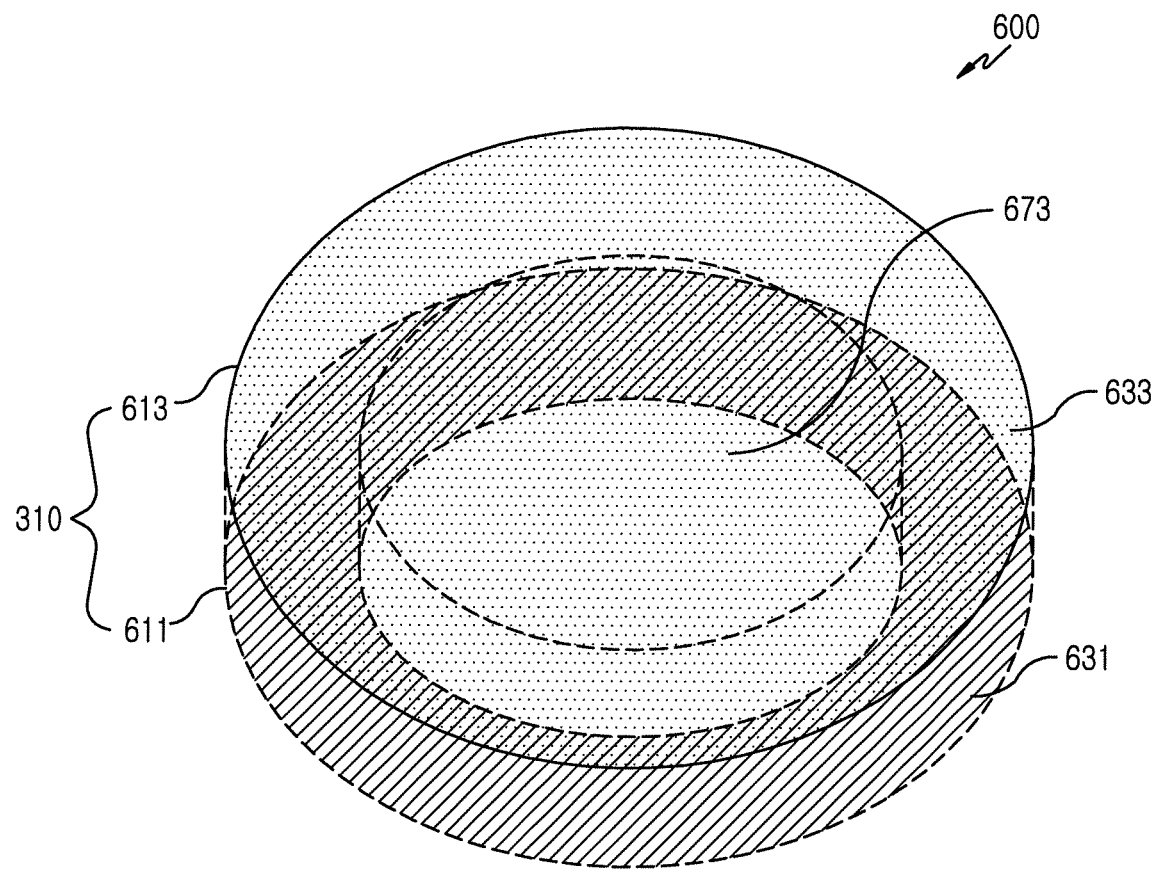
FIG. 6 illustrates an example of applying a UI for providing application information in an electronic device according to various embodiments of the present disclosure.

FIG. 6 illustrates an example 600 of applying a UI for providing application information by an electronic device (e.g., the information providing module 170) via the display 310 (e.g., the display 150) according to various embodiments of the present disclosure. Referring to FIG. 6, for example, the display 310 may output execution information and additional information via a first layer 611 and a second layer 613 located above the first layer 611. For example, at least a portion of the second layer 613 may have a degree of clearness (e.g., transparency or semi-transparency) different from that of the first layer 611. In this case, information output via the first layer 611 may be provided to a user by passing through the second layer 613.

According to the present exemplary embodiment 600, the additional area (e.g., the additional area 340) and the execution area (e.g., the execution area 370) may be output via different layers of the display 310.

For convenience of explanation, it is illustrated in FIG. 6 that the first layer 611 includes a first area 631 and the second layer 613 includes a second area 673 and a third area 633.

Referring to FIG. 6, for example, the additional area may be the first area 631, and the execution area may include at least a portion (e.g., the second area 673 and the third area 633) of the second layer 613. The third area 633 which is an area overlapping with an additional area (e.g., the first layer 611) in the second layer 613 may be output, for example, transparently or semi-transparently. In this case, additional information (e.g., the additional information 441-1 to 441-N) displayed (or to be displayed) in the additional area (e.g., the first area 631) may be provided to the user by passing through the third area 633. Although an example in which the additional area is displayed to the first layer 611 and the execution area is displayed to the second layer 613 is described above, various embodiments of the present disclosure are not limited thereto, and thus the execution area may be displayed to the first layer 611 and the additional area may be displayed to the second layer 613.

For example, if the execution area and the additional area are located in different layers, a location, size, or shape of the execution area and the additional area may be adjusted without being affected by each other. For example, according to a user input (e.g., the user input 590), a size of the execution area may be increased from a size of the second area 673 to a size of an area including the second area 673 and the third area 633, and a size of the additional area (e.g., a size of the first area 631) may be equally maintained. In this case, for example, the third area 633 of the second layer 613 may be displayed semi-transparently or transparently in a gradual manner according to a user input (e.g., a touch, hovering, or drag input).

FIG. 7A to FIG. 7E illustrate examples 710, 730, 750, 770, and 790 of applying a UI for providing application information by an electronic device (e.g., the information providing module 170) via the display 310 (e.g., the display 150) according to various embodiments of the present disclosure.

Figure 7A:
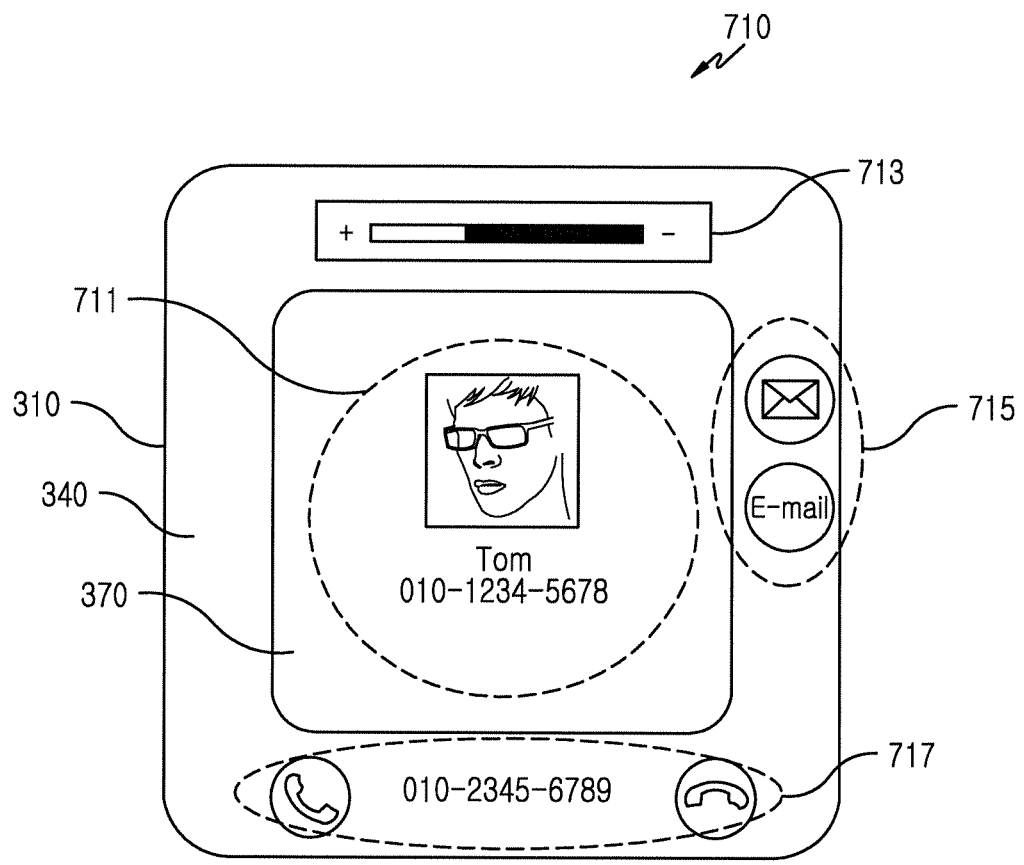
FIG. 7A to FIG. 7E illustrate an example of applying a UI for providing application information in an electronic device according to various embodiments of the present disclosure.
Figure 7B:
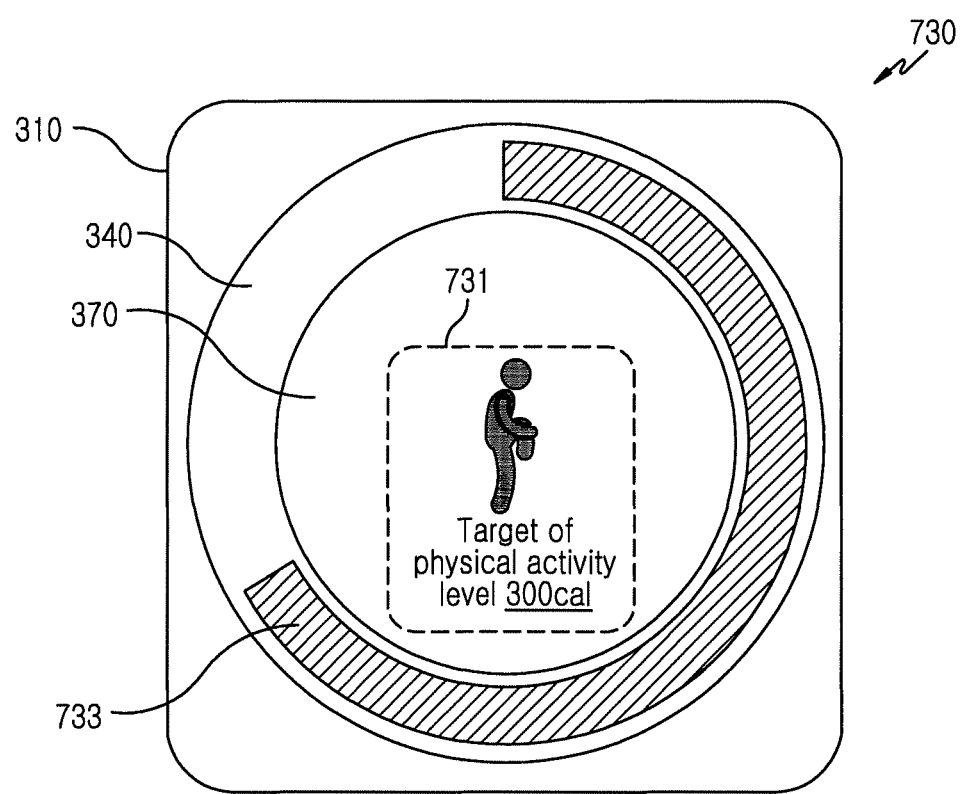
Figure 7C:
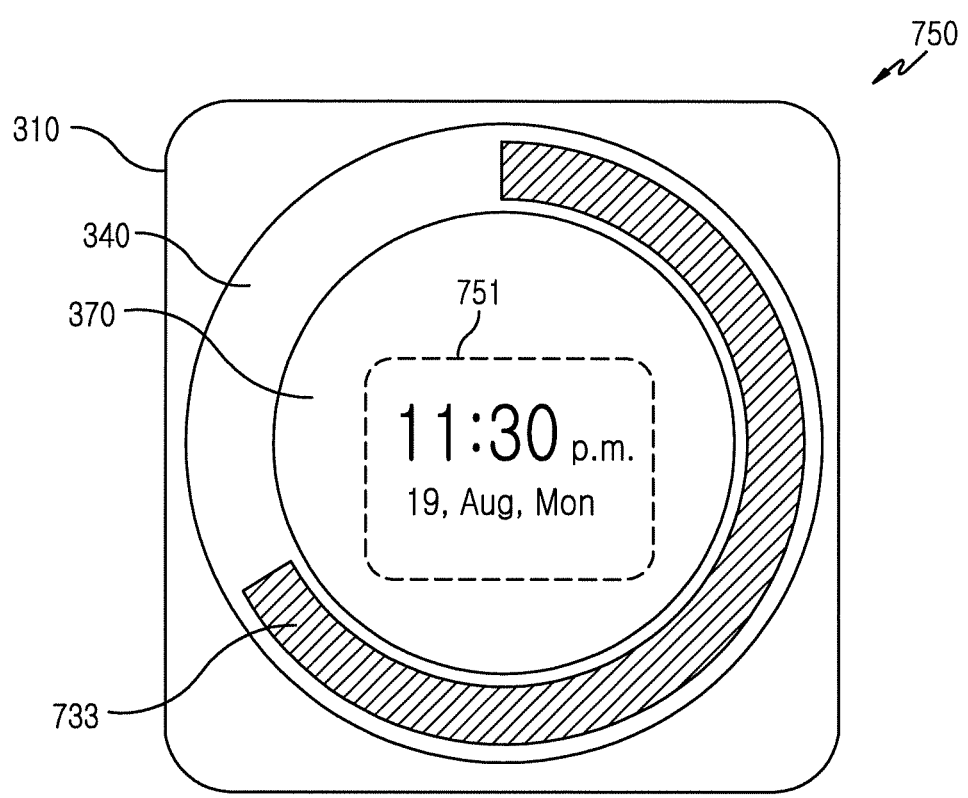
Figure 7D:
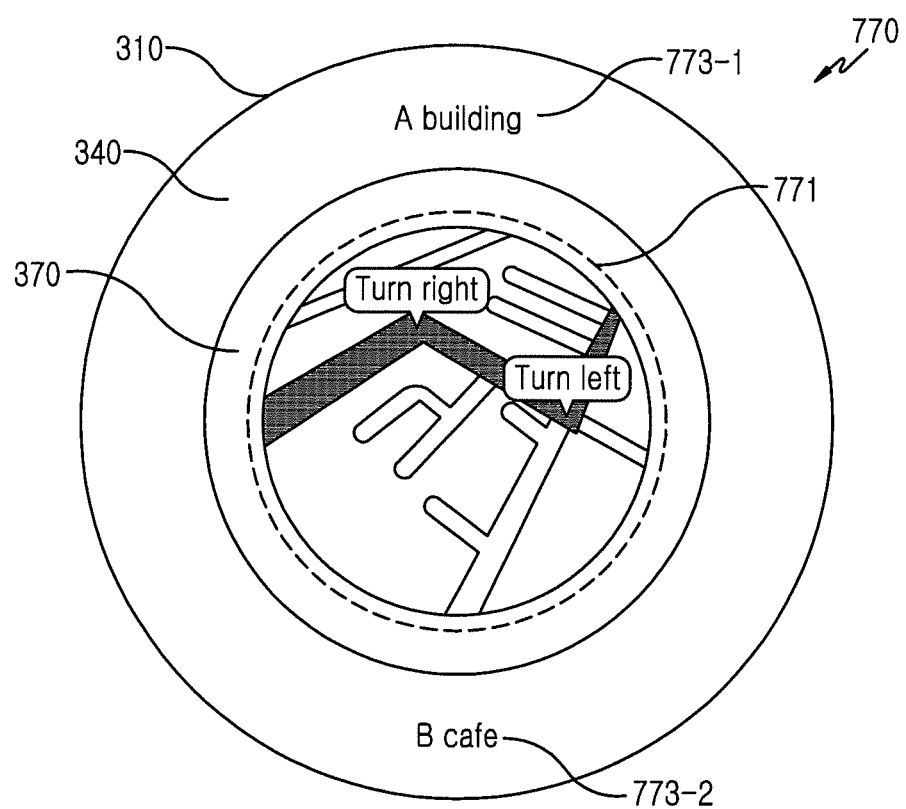

Referring to FIG. 7A, a phone application may be executed in the electronic device. In this case, information 711 (e.g., a photo, a name, or a phone number) of an in-coming caller may be provided via the execution area 370 of the display 310 as execution information of the phone application. In addition, a call volume control menu 713 capable of receiving a user input related to a call volume in a function of the phone application may be provided via the additional area 340 of the display 310.

Information related to a function of an application executed in the electronic device may be provided as additional information. For example, referring to FIG. 7A, if the phone application is executed in the electronic device and a phone event is additionally received, notification information (e.g., in-coming caller information (e.g., a phone number), a control menu for the phone event (e.g., a call response or a call end menu)) 717 corresponding to the call event may be provided via the additional area 340.

Information related to a function of an application different from a currently executed application in the electronic device 101 may be provided as the additional information via the additional area 340. For example, referring to FIG. 7A, if the phone application is under execution in the electronic device, a menu 715 capable of executing a text or e-mail application for sending a text or an e-mail to the opposite caller may be provided via the additional area 340.

Information which varies depending on situation information of the additional information may be provided to the additional area 340 as the additional information. For example, referring to FIG. 7B, if a health care application is executed in the electronic device, current physical activity level information 733 of a user may be displayed in the additional area 340 of the display 310 as the additional information. The current physical activity level information 733 may be displayed in the additional area 340 by being changed according to a change in the user's physical activity level information (e.g., walking information). For example, a colored area indicating the current physical activity level information 733 may be increased when the user's physical activity level is increased.

Upon changing the application executed in the electronic device, execution information (e.g., the execution information 471-1 to 471-N) may be changed and then may be provided via the execution area 370 of the display 310. In this case, the additional information may be provided via the additional area 340 of the display 310 without alteration. For example, referring to FIGS. 7B and 7C, the health care application may be executed in the electronic device. Physical activity level target information 731 may be provided via the execution area 370, and the current physical activity level information 733 may be provided via the additional area 340. If there is no user input for a specified time, the electronic device may transition to a sleep mode, and a time application may be executed in the electronic device. In this case, time information (e.g., information regarding a time, a date, and day of the week) 751 may be provided via the execution area 370, and the current physical activity level information 733 may be provided via the additional area 340.

The electronic device may be configured such that only one of the user inputs related to the additional area 340 or the user inputs related to the execution area 370 is acquired. For example, referring to FIG. 7C, if the electronic device is in a sleep mode, via the touch screen connected with the display, a touch input may not be acquired in the execution area 370, and a touch input for acquiring more information regarding the physical activity level information 733 may be acquired in the additional area 340.

If the execution information is modified based on situation information related to the electronic device (e.g., the electronic device 101), at least a portion of the additional information may be modified based on the modified execution information. For example, referring to FIG. 7D, if a navigation application is executed in the electronic device, map information 771 may be provided as the execution information via the execution area 370. In addition, region information 773-1 to 773-2 (e.g., tourist attraction or restaurant information) related to the map information 771 may be provided as the additional information via the additional area 340. If a location of the electronic device is modified, the map information 771 may be modified depending on the location of the electronic device. Based on the modified map information 771, the region information 773-1 to 773-2 as the additional information may be modified to region information related to the modified map information.

Execution information modified based on the modification of the additional information may be provided via the execution area 370. For example, referring to FIG. 7E, if a schedule application is executed in the electronic device, schedule information 791 may be provided as the execution information via the execution area 370 of the display 310. In addition, time information 799 may be provided as the additional information via the additional area 340 of the display 310. A sub-area (hereinafter, for convenience of explanation, a "selection area") 795 may be selected from the additional information based on a user input 797. A color of the selection area 795 may be changed based on the selection. In this case, detailed schedule information (e.g., schedule title, time or place information) 793 related to the selection area 795 may be provided to the execution area 370.

Although not shown, if the schedule application is executed in the electronic device, current time information may be provided together with the time information 799 via the additional area 340. The current time information provided to the additional area 340 may be modified according to a flow of time (e.g., situation information related to the additional information). Based on the current time information, the modified schedule information for the modified current time may be provided to the execution area 370.

Figure 7E:
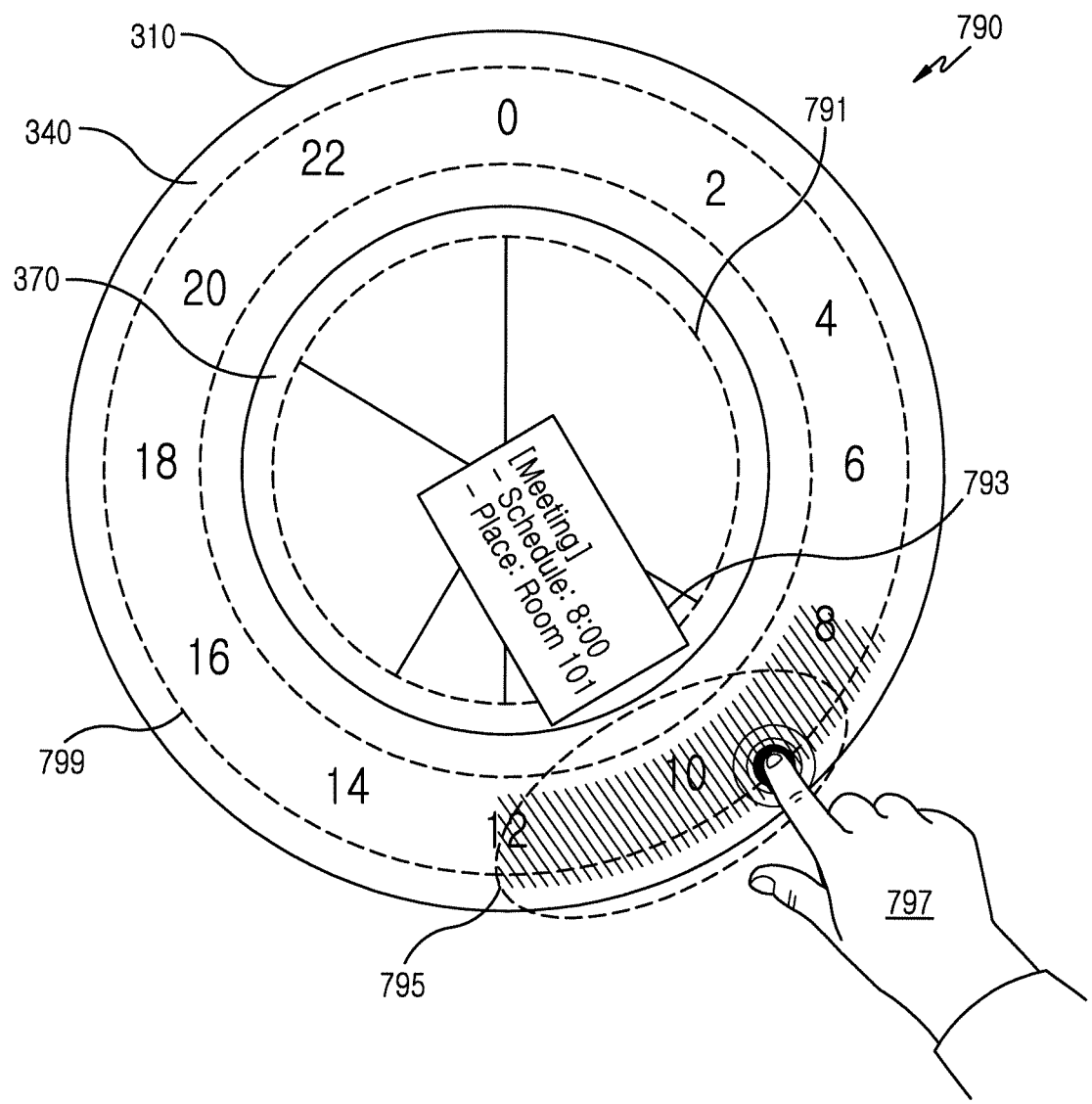

Execution information corresponding to the modified additional information may be provided to a sub-area related (or adjacent) to the additional information modified in the execution area 370. Referring to FIG. 7E, the detailed schedule information 793 corresponding to the selection area 795 in which the additional information modified in the additional area 340 is displayed may be provided to an area adjacent to the selection area 795.

According to various embodiments, the electronic device (e.g., the electronic device 101) for providing application information may include a display (e.g., the display 310) including a first specified area (e.g., the additional area 340) and a second specified area (e.g., the execution area 370) and an information providing module (e.g., the information providing module 170) for controlling the display. The information providing module may provide at least one application item (e.g., the application items 341-1 to 341-N) including information regarding a corresponding application via the first specified area, may select at least one item (e.g., the application item 341-2) from the at least one application item, may provide execution information (e.g., the execution information 471-1 to 471-N) of an application corresponding to the at least one item via the second specified area based on the selection, and may provide additional information (e.g., the additional information 441-1 to 441-N) related to the execution information via at least a portion of the first specified area based on an operation of providing the execution information.

According to various embodiments, the information providing module (e.g., the adjustment module 250) may selectively activate or deactivate the first specified area or the second specified area.

According to various embodiments, the information providing module (e.g., the adjustment module 250) may adjust at least one of a location, size, shape, and color of the first specified area or second specified area based on at least one of situation information related to the electronic device or the application, attribute information of the additional information or the execution information, a user input, and user's state information.

According to various embodiments, the information providing module (e.g., the adjustment module 250) may display the first specified area or the second specified area by increasing its size to a size of the display. For example, the information providing module may control the display such that only the additional information is displayed to the display, based on a fact that a size of the first specified area is increased to the size of the display. In addition, the display may be controlled such that only execution information of the application is displayed to the display, based on a fact that a size of the second specified area is increased to the size of the display.

According to various embodiments, the information providing module may display the increased first specified area or second specified area by decreasing a size thereof.

According to various embodiments, the information providing module (e.g., the adjustment module 250) may control, for example, the display such that a second layer (e.g., the second layer 613) having a transparency different from that of a first layer is displayed to the first layer (e.g., the first layer 611) or above the first layer.

According to various embodiments, the information providing module (e.g., the adjustment module 250) may control, for example, the display such that at least a portion of the execution information or the additional information is displayed via at least one of the first layer and the second layer.

According to various embodiments, the electronic device (e.g., the information providing module 170) for providing application information may include an application item module (e.g., the application item module 210) for providing at least one application item (e.g., the application items 341-1 to 341-N) including information regarding a corresponding application via the first specified area (e.g., the additional area 340) of the display (e.g., the display 310) operatively coupled to the electronic device (e.g., the electronic device 101), a selection module (e.g., the selection module 220) for selecting at least one item from the at least one application item, an execution module (e.g., the execution module 230) for providing execution information (e.g., the execution information 471-1 to 471-N) of an application corresponding to the at least one item via a second specified area (e.g., the execution area 370) of the display based on the selection, and an additional module (e.g., the additional module 240) for providing additional information (e.g., the additional information 441-1 to 441-N) related to the execution information via the first specified area based on the execution information.

According to various embodiments, the selection module may determine whether the at least one item is moved from the first specified area to the second specified area by a user input. For example, the selection module may select the at least one item based on the determination.

According to various embodiments, the selection module may automatically select the at least one item based on situation information related to the electronic device (e.g., the electronic device 101) or attribute information related to the application.

According to various embodiments, the at least one application item may include a first application item and a second application item. The selection module may select the first application item (e.g., an application item corresponding to a music play application) as the at least one item if the electronic device (e.g., the electronic device 101) is in a first location (e.g., a car), and may select the second application item (e.g., an application item corresponding to a schedule application) as the at least one item if the electronic device is in a second location (e.g., an office).

According to various embodiments, the execution module may provide a UI for the application as the execution information.

According to various embodiments, the execution module may automatically provide information regarding another application via the second specified area based on at least a specified time. For example, if a health care application is executed in the electronic device and a user input is not acquired by the electronic device for a specified time, the electronic device may transition to a sleep mode. In this case, the execution module may provide information (e.g., time information) regarding an application corresponding to the sleep mode via the second specified area. Additionally or alternatively, information (e.g., application item information or additional information) provided in the first specified area may be maintained when provided.

According to various embodiments, the additional information may include first information (e.g., the additional information 441-1) and second information (e.g., the additional information 441-2). The execution module may control the display such that first execution information (e.g., the execution information 471-1) corresponding to the first information is displayed in a first sub-area (e.g., the area 470-1) of the second specified area, and second execution information (e.g., the execution information 471-2) corresponding to the second information is displayed in a second sub-area (e.g., the area 470-2) of the second specified area.

According to various embodiments, the additional module may provide a control menu (e.g., the volume control menu 713) for controlling at least one function of the application as the additional information.

According to various embodiments, the additional module may determine at least one of a location, size, shape, and color of at least sub-area (e.g., the area 440) for providing the additional information in the first specified area, based on the execution information.

According to various embodiments, the additional module may provide at least one of first information corresponding to a function provided by the application and second information corresponding to a function corresponding to another application different from the previous allocation as the additional information.

According to various embodiments, the electronic device may further include a modification module (e.g., the modification module 260). The modification module may modify at least a portion of the execution information according to one of a user input related to the execution information, situation information related to the electronic device, attribute information related to the application, and user's state information, and may modify at least a portion of the additional information based on the modified execution information.

According to various embodiments, the modification module may modify at least a portion of the additional information based on at least one of a user input related to the additional information, situation information related to the electronic device or the additional information, user's state information, and may modify at least a portion of the execution information based on the modified additional information.

According to various embodiments, the electronic device (e.g., the electronic device 101) for providing application information may include an application item module (e.g., the application item module 210) for providing a plurality of application items (e.g., the application items 341-1 to 341-N) which include a first application item (e.g., the application item 341-1) including information regarding a first application and a second application item (e.g., the application item 341-2) including information regarding a second application via the first specified area (e.g., the additional area 340) of the display (e.g., the display 310) operatively coupled to the electronic device (e.g., the information providing module 170).

In addition, the electronic device (e.g., the information providing module 170) may include an execution module (e.g., the execution module 230) for providing an execution result (e.g., the execution information 471-1 to 471-N) corresponding to an application item (e.g., the application item 341-2) selected from the first application and the second application via a second specified area (e.g., the execution area 370) of the display, distinguished from the first specified area, based on the selection of the first application item or the second application item, and an additional module (e.g., the additional module 240) for providing at least one additional information (e.g., the additional information 441-1 to 441-N) corresponding to the execution result via at least sub-area of the first specified area during at least a portion of the execution result is provided via the second specified area.

According to various embodiments, the sub-area may be identical to the sub-area of the first specified area used to display the selected application item.

According to various embodiments, the additional module may control, for example, the display such that information (e.g., an application item or additional information regarding the application) regarding an application corresponding to an application item (e.g., the application item 341-1) not selected from the first application item and the second application item is displayed via another sub-area of the first specified area.

Figure 8:
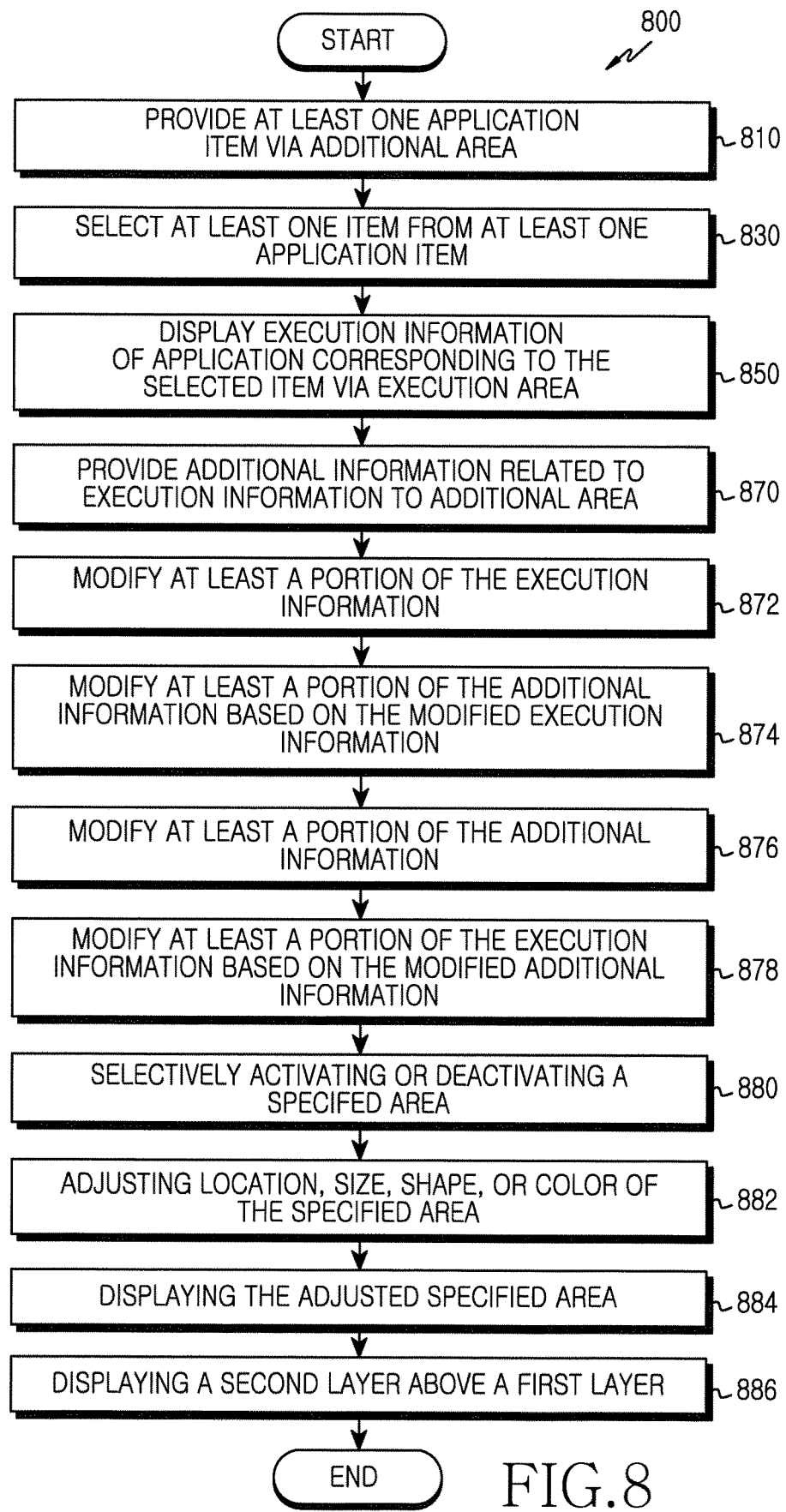
FIG. 8 illustrates a method of providing application information in an electronic device according to various embodiments of the present disclosure.

FIG. 8 illustrates a method 800 of providing application information to a display by using an electronic device (e.g., the information providing module 170) according to various embodiments of the present disclosure. For example, in an operation 810, the electronic device (e.g., the application item module 210) may provide at least one application item via an additional area (e.g., the additional area 340) of a display (e.g., the display 150). In an operation 830, the electronic device (e.g., the selection module 220) may select at least one item from the at least one application item. In an operation 850, the electronic device (e.g., the execution module 230) may display execution information of an application corresponding to the selected one item via an execution area (e.g., the execution area 370) of the display based on the operation 830. In an operation 870, the electronic device (e.g., the additional module 240) may provide additional information related to the execution information via at least a portion of the additional area based on the operation 850.

According to various embodiments, the method 800 of providing application information may include an operation of providing at least one application item (e.g., the application items 341-1 to 341-N) including information regarding a corresponding application via the first specified area (e.g., the additional area 340) of the display (e.g., the display 310) operatively coupled to the electronic device (e.g., the electronic device 101), an operation of selecting at least one item from the at least one application item, an execution module (e.g., the execution module 230) for providing execution information (e.g., the execution information 471-1 to 471-N) of an application corresponding to the at least one item via a second specified area (e.g., the execution area 370) of the display based on the selection, and an operation of providing additional information (e.g., the additional information 441-1 to 441-N) related to the execution information via the first specified area based on the execution information.

According to various embodiments, the selection operation 830 may include an operation of determining whether the at least one item is moved from the first specified area to the second specified area by a user input. For example, the at least one item may be selected based on the determination.

According to various embodiments, the selection operation 830 may include an operation of automatically selecting the at least one item based on situation information related to the electronic device (e.g., the electronic device 101) or attribute information related to the application.

According to various embodiments, the at least one application item may include a first application item and a second application item. The selection operation may include an operation of selecting the first application item (e.g., an application item corresponding to a music play application) as the at least one item if the electronic device (e.g., the electronic device 101) is in a first location (e.g., a car), and an operation of selecting the second application item (e.g., an application item corresponding to a schedule application) as the at least one item if the electronic device is in a second location (e.g., an office).

According to various embodiments, the operation 850 of displaying the execution information may include an operation of providing a UI for the application as the execution information.

According to various embodiments, the operation 850 of displaying the execution information may include an operation of automatically providing information regarding another application via the second specified area based on a specified time. For example, in this case, the provided information (e.g., the selected at least one application item or the additional information) may be provided via the first specified area.

According to various embodiments, the additional information may include first information (e.g., the additional information 441-1) and second information (e.g., the additional information 441-2). The operation 850 of displaying the execution information may include an operation of controlling the display such that first execution information (e.g., the execution information 471-1) corresponding to the first information is displayed in a first sub-area (e.g., the area 470-1) of the second specified area, and second execution information (e.g., the execution information 471-2) corresponding to the second information is displayed in a second sub-area (e.g., the area 470-2) of the second specified area.

According to various embodiments, the operation 870 of providing the additional information may include an operation of providing a control menu (e.g., the volume control menu 713) for controlling at least one function of the application as the additional information.

According to various embodiments, the operation 870 of providing the additional information may include an operation of determining at least one of a location, size, shape, and color of at least sub-area (e.g., the area 440) for providing the additional information in the first specified area, based on the execution information.

According to various embodiments, the operation 870 of providing the additional information may include an operation of providing at least one of first information corresponding to a function provided by the application and second information corresponding to a function corresponding to another application different from the previous allocation as the additional information.

According to various embodiments, the method 800 of providing the application information may further include an operation 872 of modifying at least a portion of the execution information according to one of a user input related to the execution information, a situation information related to the electronic device, an attribute information related to the application, and user's state information. The method 800 of providing the application information may further include an operation 874 of modifying at least a portion of the additional information based on the modified execution information.

According to various embodiments, the method 800 of providing the application information may further include an operation 876 of modifying at least a portion of the additional information based on at least one of a user input related to the additional information, a situation information related to the electronic device, the additional information, or user's state information. The method 800 of providing the application information may further include an operation 878 of modifying at least a portion of the execution information based on the modified additional information.

According to various embodiments, the method 800 of providing the application information may include an operation of providing a plurality of application items (e.g., the application items 341-1 to 341-N) which include a first application item (e.g., the application item 341-1) including information regarding a first application and a second application item (e.g., the application item 341-2) including information regarding a second application via the first specified area (e.g., the additional area 340) of the display (e.g., the display 310) operatively coupled to the electronic device (e.g., the information providing module 170). The method 800 of providing the application information may further include an operation of providing an execution result (e.g., the execution information 471-1 to 471-N) corresponding to an application item (e.g., the application item 341-2) selected from the first application and the second application via a second specified area (e.g., the execution area 370) of the display, distinguished from the first specified area, based on the selection of the first application item or the second application item. The method 800 of providing the application information may further include an operation of providing at least one additional information (e.g., the additional information 441-1 to 441-N) corresponding to the execution result via at least sub-area of the first specified area while at least a portion of the execution result is provided via the second specified area.

According to various embodiments, the operation 870 of providing the additional information may include an operation of displaying information (e.g., an application item or additional information regarding the application) regarding an application corresponding to an application item (e.g., the application item 341-1) not selected from the first application item and the second application item via another sub-area of the first specified area.

According to various embodiments, the method 800 of providing the application information may include an operation of providing at least one application item (e.g., the application items 341-1 to 341-N) including information regarding a corresponding application via the first specified area (e.g., the additional area 340). The method 800 of providing the application information may include an operation of selecting at least one item (e.g., the application item 341-2) from the at least one application item. The method 800 of providing the application information may include an operation of providing execution information (e.g., the execution information 471-1 to 471-N) of an application corresponding to the at least one item via a second specified area (e.g., the execution area 370) based on the selection. The method 800 of providing the application information may include an operation of providing additional information (e.g., the additional information 441-1 to 441-N) related to the execution information via the first specified area based on the operation of providing the execution information.

According to various embodiments, the method 800 of providing the application information may further include an operation 880 of selectively activating or deactivating the first specified area or the second specified area.

According to various embodiments, the method 800 of providing the application information may further include an operation 882 of adjusting at least one of a location, size, shape, and color of the first specified area or second specified area based on at least one of situation information related to the electronic device or the application, attribute information of the additional information or the execution information, a user input, and user's state information.

According to various embodiments, the method 800 of providing the application information may further include an operation of displaying the first specified area or the second specified area by increasing the size of the specified area to a size of the display. For example, only the additional information may be displayed via the display based on a fact that a size of the first specified area is increased to the size of the display, and only execution information of the application may be displayed via the display, based on a fact that a size of the second specified area is increased to the size of the display.

According to various embodiments, the method 800 of providing the application information may further include an operation of displaying 884 the increased first specified area or second specified area by decreasing a size thereof.

According to various embodiments, the method 800 of providing the application information may further include an operation 886 of displaying a second layer (e.g., the second layer 613) having a transparency different from that of a first layer to the first layer (e.g., the first layer 611) or above the first layer.

In this case, according to various embodiments, the method 800 of providing the application information may further include an operation of displaying at least a portion of the execution information or the additional information via at least one of the first layer and the second layer.

Figure 9:
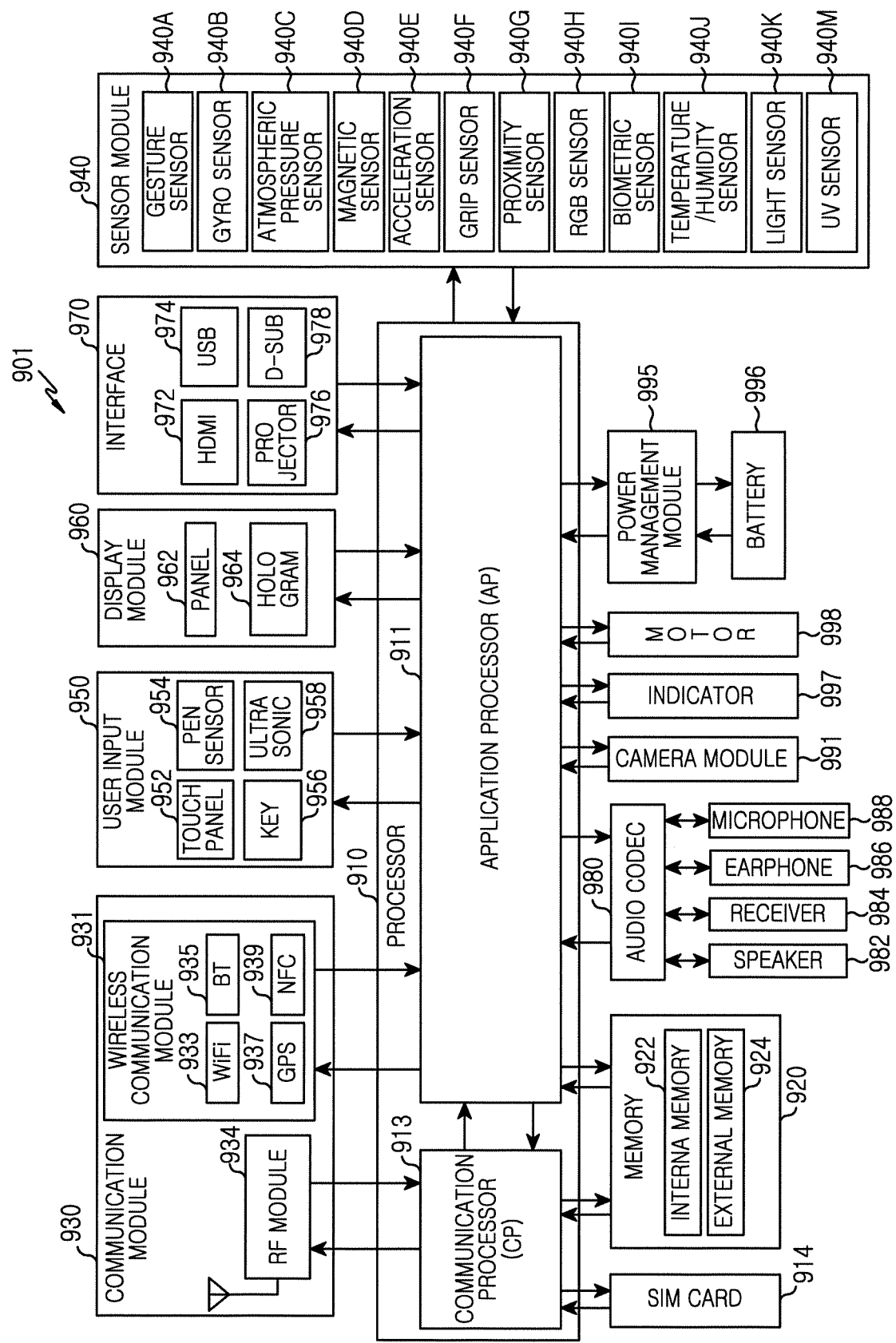
FIG. 9 illustrates a block diagram of an electronic device according to various embodiments of the present disclosure.

FIG. 9 illustrates a block diagram of an electronic device 901 according to various embodiments of the present disclosure. The electronic device 901 may be, for example, the electronic device 101 of FIG. 1. Referring to FIG. 9, the electronic device 901 includes one or more processors 910, a Subscriber Identification Module (SIM) card 914, a memory 920, a communication module 930, a sensor module 940, an input module 950, a display 960, an interface 970, an audio module 980, a camera module 991, a power management module 995, a battery 996, an indicator 997, or a motor 998.

The processor 910 (e.g., the processor 120) may include one or more Application Processors (APs) 911 or one or more Communication Processors (CPs) 913. Although it is illustrated in FIG. 9 that the AP 911 and the CP 913 are included in the processor 910, the AP 911 and the CP 913 may be included respectively in different Integrated Circuit (IC) packages. For example, the AP 911 and the CP 913 may be included in one IC package.

The AP 911 may control a plurality of hardware or software components connected to the AP 911 by driving an operating system or an application program, and may process a variety of data including multimedia data and may perform an arithmetic operation. The AP 911 may be implemented, for example, with a System on Chip (SoC). For example, the processor 910 may further include a Graphic Processing Unit (GPU, not shown).

The CP 913 may perform a function of managing a data link and changing communication protocol in a communication between the electronic device 901 (e.g., the electronic device 101) and different electronic devices (e.g., the electronic device 102, the electronic device 104, or the server 106) connected through a network. The CP 913 may be implemented, for example, with an SoC. For example, the CP 913 may perform at least a part of a multimedia control function. The CP 913 may identify and authenticate a user equipment in a communication network, for example, by using a subscriber identity module (e.g., the SIM card 914). The CP 913 may provide a service including a voice call, a video call, a text message, packet data, or the like to a user.

In addition, the CP 913 may control a data transmission/reception of the communication module 930. Although components such as the CP 913, the power management module 995, the memory 920, and the like, are illustrated as separate components in FIG. 9, the AP 911 may also be implemented such that at least one part (e.g., the CP 913) of the aforementioned components is included.

The AP 911 or the CP 913 may load an instruction or data, which is received from each non-volatile memory connected thereto or at least one of different components, to a volatile memory and may process the instruction or data. The AP 911 or the CP 913 may store data, which is received from at least one of different components or generated by at least one of different components, into the non-volatile memory.

The SIM card 914 may be a card in which a SIM is implemented, and may be inserted to a slot formed at a specific location of the electronic device. The SIM card 914 may include unique identification information (e.g., an Integrated Circuit Card IDentifier (ICCID)) or subscriber information (e.g., an International Mobile Subscriber Identity (IMSI)).

The memory 920 (e.g., the memory 130) may include an internal memory 922 or an external memory 924. The internal memory 922 may include, for example, at least one of a volatile memory (e.g., a Dynamic RAM (DRAM), a Static RAM (SRAM), a Synchronous Dynamic RAM (SDRAM), etc.) or a non-volatile memory (e.g., a One Time Programmable ROM (OTPROM), a Programmable ROM (PROM), an Erasable and Programmable ROM (EPROM), an Electrically Erasable and Programmable ROM (EEPROM), a Mask ROM, a Flash ROM, a NAND flash memory, a NOR flash memory, etc.). The internal memory 922 may have a form of a Solid State Drive (SSD). The external memory 924 may be a flash drive, and may further include, for example. Compact Flash (CF), Secure Digital (SD), Micro Secure Digital (Micro-SD), Mini Secure digital (Mini-SD), extreme Digital (xD), memory stick, and the like. The external memory 924 may be operatively coupled to the electronic device 901 via various interfaces. According to certain embodiments, the electronic device 901 may further include a storage unit (or a storage medium) such as a hard drive.

The communication module 930 (e.g., the communication interface 160) may include a wireless communication module 931 or a Radio Frequency (RF) module 934. The wireless communication module 931 may include, for example, a Wi-Fi 933, a BlueTooth (BT) 935, a Global Positioning System (GPS) 937, or a Near Field Communication (NFC) 939. Additionally or alternatively, although not shown, the wireless communication module 931 may include an ultrasonic module. For example, the wireless communication module 931 may provide a wireless communication function by using a radio frequency. Additionally or alternatively, the wireless communication module 931 may include a network interface (e.g., a LAN card), modem, or the like for connecting the electronic device 901 to a network (e.g., Internet, LAN, WAN, telecommunication network, cellular network, satellite network, POTS, etc.).

The RF module 934 may serve to transmit/receive data, for example, to transmit/receive an RF signal. Although not shown, the RF module 934 may include, for example, a transceiver, a Power Amp Module (PAM), a frequency filter, a Low Noise Amplifier (LNA), and the like. The RF module 934 may further include a component for transmitting/receiving a radio wave on a free space in wireless communication, for example, a conductor, a conducting wire, etc.

The sensor module 940 may measure a physical quantity or detect an operation state of the electronic device 901, and thus may convert the measured or detected information into an electric signal. The sensor module 940 may include, for example, at least one of a gesture sensor 940A, a gyro sensor 940B, a pressure sensor 940C, a magnetic sensor 940D, an acceleration sensor 940E, a grip sensor 940F, a proximity sensor 940G, a color sensor 940H (e.g., a Red, Green, Blue (RGB) sensor), a bio sensor 940I, a temperature/humidity sensor 940J, an illumination sensor 940K, and an Ultra Violet (UV) sensor 940M. Additionally or alternatively, the sensor module 940 may include, for example, an E-node sensor (not shown), an ElectroMyoGraphy (EMG) sensor (not shown), an ElectroEncephaloGram (EEG) sensor (not shown), an ElectroCardioGram (ECG) sensor (not shown), a fingerprint sensor, and the like. The sensor module 940 may further include a control circuit for controlling at least one or more sensors included therein.

The input module 950 may include a touch panel 952, a (digital) pen sensor 954, a key 956, or an ultrasonic input unit 958. The touch panel 952 may recognize a touch input, for example, by using at least one of an electrostatic type, a pressure-sensitive type, and an ultrasonic type. The touch panel 952 may further include a control circuit. In case of the electrostatic type, not only a physical contact but also a proximity recognition is possible. The touch penal 952 may further include a tactile layer. In this case, the touch panel 952 may provide the user with a tactile reaction.

The (digital) pen sensor 954 may be implemented, for example, by using the same or similar method of receiving a touch input of the user or by using an additional sheet for recognition. The key 956 may be, for example, a physical button, an optical key, a keypad, or a touch key. The ultrasonic input unit 958 is a device by which a user equipment detects a sound wave through a microphone (e.g., a microphone 988) by using a pen which generates an ultrasonic signal, and is a device capable of radio recognition. According to certain embodiments, the electronic device 901 may use the communication module 930 to receive a user input from an external device (e.g., a network, a computer, or a server) connected thereto.

The display 960 (e.g., the display 150) may include a panel 962, a hologram 964, or a projector 966. The panel 962 may be, for example, a Liquid-Crystal Display (LCD), an Active-Matrix Organic Light-Emitting Diode (AM-OLED), and the like. The panel 962 may be implemented, for example, in a flexible, transparent, or wearable manner. The panel 962 may be constructed as one module with the touch panel 952. The hologram 964 may use an interference of light and show a stereoscopic image in the air. The projector 966 may display an image by projecting a light beam onto a screen. The screen may be located, for example, inside or outside the electronic device 901. The display 960 may further include a control circuit for controlling the panel 962, the hologram 964, or the projector 966.

The interface 970 may include, for example, a High-Definition Multimedia Interface (HDMI) 972, a Universal Serial Bus (USB) 974, an optical communication interface 976, or a D-subminiature (D-sub) 978. The interface 970 may be included, for example, in the communication interface 160 of FIG. 1. Additionally or alternatively, the interface 970 may include, for example, Mobile High-definition Link (MHL) (not shown), Secure Digital (SD)/Multi-Media Card (MMC) (not shown) or Infrared Data Association (IrDA) (not shown).

The audio module 980 may bilaterally convert a sound and electronic signal. At least some components of the audio module 908 may be included in, for example, the input/output interface 140 of FIG. 1. The audio module 980 may convert sound information which is input or output, for example, through a speaker 982, a receiver 984, an earphone 986, the microphone 988, and the like.

The camera module 991 is a device for image and video capturing, and may include one or more image sensors (e.g., a front sensor or a rear sensor), a lens (not shown), an Image Signal Processor (ISP) (not shown), or a flash (not shown, e.g., LED or xenon lamp).

The power management module 995 may manage a power of the electronic device 901. Although not shown, the power management module 995 may include, for example, a Power Management Integrated Circuit (PMIC), a charger Integrated Circuit (IC), or a battery fuel gauge.

The PMIC may be placed, for example, inside an IC or SoC semiconductor. Charging may be classified into wired charging and wireless charging. The charger IC may charge a battery, and may avoid an over-voltage or over-current flow from a charger. The charger 1C may further include a charger IC for at least one of the wired charging and the wireless charging. The wireless charging may be classified into, for example, a magnetic resonance type, a magnetic induction type, and an electromagnetic type. An additional circuit for the wireless charging, for example, a coil loop, a resonant circuit, a rectifier, and the like, may be added.

The battery gauge may measure, for example, a residual quantity of the battery 996 and a voltage, current, and temperature during charging. The battery 996 may store or generate an electricity, and may supply a power to the electronic device 901 by using the stored or generated electricity. For example, the battery 996 may include a rechargeable battery or a solar battery.

The indicator 997 may indicate a specific state, for example, a booting state, a message state, a charging state, and the like, of the electronic device 901 or a part thereof (e.g., the AP 911). The motor 998 may convert an electric signal into a mechanical vibration. Although not shown, the electronic device 901 may include a processing unit (e.g., a GPU) for supporting a mobile TV. The processing unit for supporting the mobile TV may process media data according to a protocol of, for example, Digital Multimedia Broadcasting (DMB), Digital Video Broadcasting (DVB), media flow, and the like.

Each of the aforementioned components of the electronic device according to the present disclosure may consist of one or more components, and names thereof may vary depending on a type of electronic device. The electronic device according to the present disclosure may include at least one of the aforementioned components. Some of the components may be omitted, or additional other components may be further included. In addition, some of the components of the electronic device according to the present disclosure may be combined and constructed as one entity, so as to equally perform functions of corresponding components before combination.

A term "module" used in the present disclosure may imply a unit including, for example, one of hardware, software, and firmware or a combination of two or more of them. The "module" may be interchangeably used with a term such as a unit, a logic, a logical block, a component, a circuit, and the like. The "module" may be a minimum unit of an integrally constituted component or may be a part thereof. The "module" may be a minimum unit for performing one or more functions or may be a part thereof. The "module" may be mechanically or electrically implemented. For example, the "module" of the present disclosure may include at least one of an Application-Specific Integrated Circuit (ASIC) chip, a Field-Programmable Gate Arrays (FPGAs), and a programmable-logic device, which perform certain operations.

According to various embodiments, at least some parts of a device (e.g., modules or functions thereof) or method (e.g., operations) of the present disclosure may be implemented with an instruction stored in a computer-readable storage media for example. If the instruction is executed by one or more processors (e.g., the processor 210), the one or more processors may perform a function corresponding to the instruction. The computer-readable storage media may be, for example, the memory 220. At least some parts of the programming module may be implemented (e.g., executed), for example, by the processor 210. At least some parts of the programming module may include modules, programs, routines, sets of instructions, processes, and the like, for performing one or more functions.

The computer readable recording medium may be a hardware device configured particularly to store and perform a program instruction (e.g., program module), for example, a hard disk, a magnetic medium such as a floppy disc and a magnetic tape, an optical storage medium such as a Compact Disc-ROM (CD-ROM) or a Digital Versatile Disc (DVD), a magnetic-optic medium such as a floptical disc, a Read Only Memory (ROM), a Random Access Memory (RAM), a flash memory, and the like. An example of the program instruction includes not only a machine language created by a compiler but also a high-level language executable by a computer by using an interpreter or the like. The aforementioned hardware device may be configured to operate as one or more software modules to perform the operation of the present disclosure, and the other way around is also possible.

The module or programming module according to the present disclosure may further include at least one or more components among the aforementioned components, or may omit some of them, or may further include additional other components. Operations performed by a module, programming module, or other components of the present disclosure may be executed in a sequential, parallel, repetitive, or heuristic manner. In addition, some of the operations may be executed in a different order or may be omitted, or other operations may be added.

According to various embodiments, in a storage medium having instructions stored therein, when the instructions are executed by at least one processor, the processor is configured to perform at least one operation. The at least one operation includes providing at least one application item including information regarding a corresponding application, by using a first specified area of a display operatively coupled to an electronic device, identifying at least one item from the at least one application item, providing execution information of an application corresponding to the at least one item via a second specified area of the display based on the identifying, and providing additional information related to the execution information via the first specified area, based on the execution information.

While the present disclosure has been shown and described with reference to certain embodiments thereof, it will be understood by those skilled in the art that various changes in form and details may be made therein without departing from the spirit and scope of the disclosure as defined by the appended claims. Therefore, the scope of the present disclosure is defined not by the detailed description of the present disclosure but by the appended claims, and all differences within the scope will be construed as being included in the present disclosure.

A method and apparatus for providing application information according to various embodiments can simultaneously display various types of information related to an application via a display for example. Therefore, a user convenience is improved when a user uses the application.

A method and apparatus for providing application information according to various embodiments can simultaneously provide various types of information related to an application without an additional input of a user for example. Therefore, the application information which is intended to be confirmed by the user can be easily provided.

What is claimed is:

1. A smart watch comprising:
   a display;
   at least one sensor configured to obtain activity information related to a physical activity of a user; and
   a processor configured to:
      display a plurality of items corresponding to a plurality of applications on a first area of the display of the smart watch;
      receive an input for executing an activity application among the plurality of applications;
      in response to receiving the input, execute the activity application;
      display, on a second area of the display of the smart watch, first information corresponding to a target activity amount that is set in the activity application;
      display, on the first area of the display of the smart watch, second information indicating the activity information obtained from the at least once sensor; and
      replace the first information displayed on the first area of the display of the smart watch to another information, while maintaining the second information displayed on the first area,
   wherein the first area is adjacent to the second area, and is arranged to surround the second area.

2. The smart watch of claim 1, wherein the first information comprises information related to calories.

3. The smart watch of claim 1, wherein the second information comprises current activity information obtained from the at least one sensor.

4. The smart watch of claim 3, wherein the second information comprises a graphic effect indicating the current activity information, and
   wherein an area of the graphic effect is increased based on the current activity information.

5. The smart watch of claim 1, wherein a shape of the display is a circular shape and the first area and the second area are divided into an outer region of a circle and an inner region of the circle on a screen of the display.

6. The smart watch of claim 1, wherein a shape of the first area and the second area correspond to a shape of the display, wherein the shape of the display comprises a circular shape or a square shape.

7. The smart watch of claim 1, wherein the first information corresponding to the target activity amount that is set in the activity application is changed to information other than the first information when the activity application is changed to another application.

8. A method for providing information in a smart watch, the method comprising:
   displaying a plurality of items corresponding to a plurality of applications;
   receiving an input for executing an activity application among the plurality of applications;
   in response to receiving the input, executing the activity application;
   displaying, on a second area of the smart watch, first information corresponding to a target activity amount that is set in the activity application;
   displaying, on a first area of the smart watch, second information indicating activity information obtained from at least one sensor of the smart watch; and
   replacing the first information displayed on the first area to another information, while maintaining the second information displayed on the first area,
   wherein the first area is adjacent to the second area and is arranged to surround the second area.

9. The method of claim 8, wherein the first information comprises information related to calories.

10. The method of claim 8, wherein the second information comprises current activity information obtained from the at least one sensor.

11. The method of claim 10, wherein the second information comprises a graphic effect indicating the current activity information, and
    wherein an area of the graphic effect is increased based on the current activity information.

12. The method of claim 8, wherein a shape of a display is a circular shape and the first area and the second area are divided into an outer region of a circle and an inner region of the circle on a screen of the display.

13. The method of claim 8, wherein a shape of the first area and the second area correspond to a shape of a display, wherein the shape of the display comprises a circular shape or a square shape.

14. The method of claim 8, wherein the first information corresponding to the target activity amount that is set in the activity application is changed to information other than the first information when the activity application is changed to another application.

* * * * *